United States Patent
Saha et al.

(10) Patent No.: US 7,790,707 B2
(45) Date of Patent: Sep. 7, 2010

(54) S1P RECEPTOR MODULATING COMPOUNDS AND USE THEREOF

(75) Inventors: Ashis Saha, Stow, MA (US); Xiang Yu, Acton, MA (US); Mercedes Lobera, Bolton, MA (US); Jian Lin, Walpole, MA (US); Srinivasa R. Cheruku, Lexington, MA (US); Oren Becker, Mevaseret Zion (IL); Yael Marantz, Kadima (IL); Nili Schutz, Tel-Aviv (IL)

(73) Assignee: EPIX Pharmaceuticals Inc., Lexington, MA (US)

( * ) Notice: Subject to any disclaimer, the term of this patent is extended or adjusted under 35 U.S.C. 154(b) by 0 days.

(21) Appl. No.: 11/726,356

(22) Filed: Mar. 21, 2007

(65) Prior Publication Data

US 2008/0015177 A1 Jan. 17, 2008

Related U.S. Application Data

(60) Provisional application No. 60/784,548, filed on Mar. 21, 2006.

(51) Int. Cl.
- *A61K 31/397* (2006.01)
- *A61K 31/4166* (2006.01)
- *C07D 205/04* (2006.01)
- *C07D 403/02* (2006.01)
- *C07D 403/06* (2006.01)

(52) U.S. Cl. ............... 514/210.01; 514/210.17; 514/210.18; 514/210.2; 514/392; 548/314.7; 548/316.4; 548/325.5; 548/950; 548/953

(58) Field of Classification Search ........... 514/386, 514/392; 548/317.1, 314.7, 311.1, 321.1
See application file for complete search history.

(56) References Cited

U.S. PATENT DOCUMENTS

| | | | |
|---|---|---|---|
| 3,329,781 A | 7/1967 | Wiser | |
| 4,767,896 A | 8/1988 | Nigg et al. | |
| 5,145,865 A | 9/1992 | Fujii et al. | |
| 5,614,531 A | 3/1997 | Juraszyk et al. | |
| 5,880,284 A * | 3/1999 | Himmelsbach et al. | 546/133 |
| 6,384,061 B1 * | 5/2002 | Lee et al. | 514/341 |
| 6,411,326 B1 | 6/2002 | Tabata | |
| 2002/0156074 A1 | 10/2002 | Barvian et al. | |
| 2002/0183519 A1 | 12/2002 | Nar et al. | |
| 2005/0014725 A1 | 1/2005 | Mi et al. | |
| 2005/0113283 A1 | 5/2005 | Solo-Codero et al. | |
| 2006/0135786 A1 | 6/2006 | Saha et al. | |
| 2007/0173487 A1 | 7/2007 | Saha et al. | |
| 2008/0015177 A1 | 1/2008 | Saha et al. | |
| 2008/0027036 A1 | 1/2008 | Burli et al. | |
| 2008/0064677 A9 | 3/2008 | Saha et al. | |

FOREIGN PATENT DOCUMENTS

| | | |
|---|---|---|
| EP | 1553075 | 7/2005 |
| JP | 10204059 | 4/1998 |
| JP | 10-204059 | 8/1998 |
| WO | 2002064616 | 8/2002 |
| WO | WO 03/061567 A2 | 7/2003 |
| WO | WO 03/062252 A1 | 7/2003 |
| WO | WO 03/105771 A2 | 12/2003 |
| WO | 2004048383 | 6/2004 |
| WO | 2004062663 | 7/2004 |
| WO | 2004113330 | 12/2004 |
| WO | 2005020882 | 3/2005 |
| WO | WO 2005/020882 A3 | 3/2005 |
| WO | WO 2006/064757 A1 | 6/2006 |
| WO | WO 2007/061458 A2 | 5/2007 |
| WO | WO 2007/109334 A2 | 9/2007 |
| WO | WO 2009/038759 A2 | 3/2009 |

OTHER PUBLICATIONS

ISA/US International Search Report, dated Sep. 11, 2007, for International Application No. PCT/US2007/007037, filed Mar. 21, 2007.
Traynor et al., 1995, "Modulation by μ-opioid agonists of guanosine-5'-O-(3-[$^{35}$S]thio)triphosphate binding to membranes from human neuroblastoma SH-SY5Y cells," Molecular Pharmacology, 47, 848-854.
Zemann et al., 2006, "Sphingosine kinase type 2 is essential for lymphopenia induced by the immunomodulatory drug FTY720," Blood, 107(4), 1454-1458.
Pan et al., 2006, A monoselective sphingosine-1-phosphate receptor-1 agonist prevents allograft rejection in a stringent rat heart transplantation model. Chemistry & Biology. 13, 1227-1234.
Abdel-Rahman, T.M., 1998, "Synthesis and Antimicrobial Activity of Some new Thiophene-2-Sulphonyl, Amino Acids and Their Peptide Derivatives," Mans.Sci.Bull. (A Chem.) vol. 25(1), Jun. 1998.

* cited by examiner

*Primary Examiner*—Yong Chu
(74) *Attorney, Agent, or Firm*—McDonnell Boehnen Hulbert & Berghoff

(57) ABSTRACT

The present invention relates to compounds that have activity as S1P receptor modulating agents and the use of such compounds to treat diseases associated with inappropriate S1P receptor activity. In certain embodiments, the compounds of the invention relate to aryl oxoimidazolidinyls.

11 Claims, No Drawings

S1P RECEPTOR MODULATING COMPOUNDS AND USE THEREOF

RELATED APPLICATIONS

This application claims the benefit of priority under 35 U.S.C. 119(e) to copending U.S. Provisional Application No. 60/784,548, filed Mar. 21, 2006, the entire contents of which are hereby incorporated by reference.

FIELD OF THE INVENTION

The present invention relates to compounds that have activity as S1P receptor modulating agents and the use of such compounds to treat diseases associated with inappropriate S1P receptor activity.

BACKGROUND OF THE INVENTION

Sphingosine-1-phosphate (S1P) has been demonstrated to induce many cellular effects, including those that result in platelet aggregation, cell proliferation, cell morphology, tumor cell invasion, endothelial cell chemotaxis and endothelial cell in vitro angiogenesis. S1P receptors are therefore good targets for therapeutic applications such as wound healing and tumor growth inhibition. S1P signals cells in part via a set of G protein-coupled receptors named S1P1, S1P2, S1P3, S1P4, and S1P5 (formerly called EDG-1, EDG-5, EDG-3, EDG-6, and EDG-8, respectively). These receptors share 50-55% amino acid and cluster identity with three other receptors (LPA1, LPA2, and LPA3 (formerly EDG-2, EDG-4 and EDG-7)) for the structurally-related lysophosphatidic acid (LPA).

A conformational shift is induced in the G-Protein Coupled Receptor (GPCR) when the ligand binds to that receptor, causing GDP to be replaced by GTP on the α-subunit of the associated G-proteins and subsequent release of the G-proteins into the cytoplasm. The α-subunit then dissociates from the βγ-subunit, and each subunit can then associate with effector proteins, which activate second messengers leading to a cellular response. Eventually the GTP on the G-proteins is hydrolyzed to GDP, and the subunits of the G-proteins re-associate with each other and then with the receptor. Amplification plays a major role in the general GPCR pathway. The binding of one ligand to one receptor leads to the activation of many G-proteins, each capable of associating with many effector proteins, leading to an amplified cellular response.

S1P receptors make good drug targets, because individual receptors are both tissue- and response-specific. Tissue specificity of the S1P receptors is important, because development of an agonist or antagonist selective for one receptor localizes the cellular response to tissues containing that receptor, limiting unwanted side effects. Response specificity of the S1P receptors is also important because it allows for development of agonists or antagonists that initiate or suppress certain cellular responses without affecting other things. For example, the response specificity of the S1P receptors could allow for an S1P mimetic that initiates platelet aggregation without affecting cell morphology.

S1P is formed as a metabolite of sphingosine in its reaction with sphingosine kinase, and is abundantly stored in platelet aggregates where high levels of sphingosine kinase exist and sphingosine lyase is lacking. S1P is released during platelet aggregation, accumulates in serum and is also found in malignant ascites. S1P biodegradation most likely proceeds via hydrolysis by ectophosphohydrolases, specifically the sphingosine 1-phosphate phosphohydrolases.

SUMMARY OF THE INVENTION

The present invention relates to the use of new compositions which include S1P modulators, e.g., agonists, partial agonists, inverse agonists and antagonists, for treating, preventing or curing various S1P receptor-related conditions. The invention features compounds which are S1P receptor modulators; in an embodiment, such compounds include those having the formula

(I)

and pharmaceutically acceptable salts thereof;

wherein, p and q may independently be 0, 1, 2, 3 or 4; Z may independently be O, $NR^2$, S, S(O), $S(O)_2$, $S(O)_2NR^2$, $(CR^3R^4)_n$, C=O, C=S, C=N—$R^2$ or a direct bond; n may be 0, 1, 2, 3 or 4; $R^2$ may be hydrogen, hydroxyl, $S(O)_2$, C=O, C=S, C=NH, $C_{1-6}$ alkyl, $C_{1-5}$ alkoxy, $C_{1-5}$ alkylthio, halo-substituted $C_{1-6}$ alkyl, halo-substituted $C_{1-5}$ alkoxy, aryl, or heteroaryl; $R^3$ and $R^4$ may independently be hydrogen, halo, hydroxyl, cyano, $C_{1-6}$ alkyl, $C_{1-5}$ alkoxy, $C_{1-5}$ alkylthio, halo-substituted $C_{1-6}$ alkyl, halo-substituted $C_{1-5}$ alkoxy, aryl, or heteroaryl; or $R^3$ and $R^4$, taken together, may form "C=O".

$R^1$ may be $C_{1-6}$ alkyl, $C_{2-6}$ alkenyl, $C_{2-6}$ alkynyl, $C_{3-6}$ cycloalkyl, $C_{1-5}$ alkoxy, aryl or heteroaryl. Substituted groups above may each be substituted with hydroxyl, halogen, cyano, $C_{1-5}$ alkoxy, $C_{3-6}$ cycloalkyl, aryl and/or heteroaryl groups, said aryl and heteroaryl groups may be optionally substituted with 1-5 substituents independently selected from the group consisting of hydroxyl, halogen, cyano, $C_{1-6}$ alkyl, $C_{1-5}$ alkylthio, $C_{1-5}$ alkoxy, and $C_{3-6}$ cycloalkyl.

X may be $WC(O)OR^{5a}$, $WP(O)R^{5b}R^{5c}$, $WS(O)_2OH$, $WS(O)_2NH_2$, $WCONHSO_3H$ or 1H-tetrazol-5-yl. W may be a direct bond, oxygen or $C_{1-4}$ alkylene with substituents independently selected from the group consisting of halo, hydroxyl, cyano, amino, alkylamino, aryl amino, heteroaryl amino groups, $C_{1-4}$ alkoxy and $CO_2H$; $R^{5a}$ is hydrogen or $C_{1-4}$ alkyl; $R^{5b}$ and $R^{5c}$ are independently hydrogen, hydroxyl, $C_{1-4}$ alkyl, or halo substituted $C_{1-4}$ alkyl.

Y may be a bond or

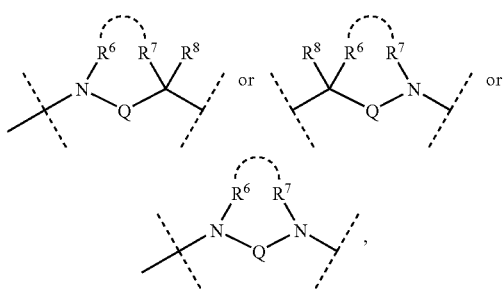

wherein Q is a direct bond, C=O, C=S, $SO_2$, $C(O)NR^9$, or $(CR^9R^{10})_m$; m is 0, 1, 2 or 3; and $R^6$ and $R^7$ may independently be hydrogen, halo, hydroxyl, cyano, $C_{1-6}$ alkyl, $C_{1-5}$ alkylthio, $C_{1-5}$ alkoxy, halo-substituted $C_{1-6}$ alkyl or halo-substituted $C_{1-5}$ alkoxy; or $R^6$ and $R^7$ may be joined together with the atoms to which they are attached to form a 4- to 7-membered ring, or $R^6$ is an alkylene group with the omega end of said alkylene group attached to ring A. $R^8$ may independently be hydrogen, halogen, hydroxyl, amino, cyano, $C_{1-6}$ alkyl, $C_{1-5}$ alkylthio, $C_{1-5}$ alkoxy, halo-substituted $C_{1-6}$ alkyl, or halo-substituted $C_{1-5}$ alkoxy.

$R^9$ and $R^{10}$ may independently be hydrogen, halo, hydroxyl, cyano, $C_{1-6}$ alkyl, $C_{1-5}$ alkoxy, $C_{1-5}$ alkylthio, halo-substituted $C_{1-6}$ alkyl, halo-substituted $C_{1-5}$ alkoxy, or —$CO_2R^{5a}$. A may be aryl or heteroaryl, either of which may optionally be substituted with 1, 2, or 3 substituents such as halo, hydroxyl, cyano, $C_{1-6}$ alkyl, $C_{1-5}$ alkylthio, $C_{1-5}$ alkoxy, halo-substituted $C_{1-6}$ alkyl, or halo-substituted $C_{1-5}$ alkoxy.

B has the formula:

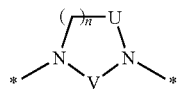

in which, the asterisks indicate the point of attachment in formula I, n is 1 or 2; U is $CH_2$, $C(H)CH_3$, $C(CH_3)_2$, $C(H)(CF_3)$, $C(CF_3)_2$, or $C(=O)$; and V is $C(=O)$, $C(=S)$, S, $S(=O)$ or $S(=O)_2$.

In one aspect, the present invention provides methods for modulating S1P-1 receptor mediated biological activity. The present invention also provides methods for using S1P-1 modulators (i.e., agonists or antagonists) in treating or preventing diseases such as ovarian cancer, peritoneal cancer, endometrial cancer, cervical cancer, breast cancer, colorectal cancer, uterine cancer, stomach cancer, small intestine cancer, thyroid cancer, lung cancer, kidney cancer, pancreas cancer and prostate cancer, acute lung diseases, adult respiratory distress syndrome ("ARDS"), acute inflammatory exacerbation of chronic lung diseases such as asthma, surface epithelial cell injury such as transcorneal freezing or cutaneous burns, and cardiovascular diseases such as ischemia in a subject in need of such treatment or prevention.

In another aspect, the invention provides methods for using S1P-1 modulators in treating or preventing disorders such as, but not limited to, vasoconstriction in cerebral arteries, autoimmune and related immune disorders including systemic lupus erythematosus, inflammatory bowel diseases such as Crohn's disease and ulcerative colitis, type I diabetes, uveitis, psoriasis, myasthenia gravis, rheumatoid arthritis, non-glomerular nephrosis, hepatitis, Behçet's disease, glomerulonephritis, chronic thrombocytopenic purpura, hemolytic anemia, hepatitis and Wegner's granuloma.

In still another aspect, the invention provides methods for using S1P-1 modulators to treat or prevent a disease or disorder in a subject, comprising administering to a subject in need of such treatment or prevention a therapeutically effective amount of an S1P-1 modulator, e.g., an agonist, that stimulates the immune system. In certain embodiments, the subject is afflicted by an infectious agent. In other embodiments, the subject is immunocompromised.

In still another aspect, the present invention provides a method of modulating an S1P-1 receptor-mediated biological activity in a cell. A cell expressing the S1P-1 receptor is contacted with an amount of an S1P-1 receptor modulator sufficient to modulate the S1P-1 receptor mediated biological activity.

In yet another aspect, the present invention provides a method for modulating an S1P-1 receptor mediated biological activity in a subject. In such a method, an amount of a modulator of the S1P-1 receptor effective to modulate an S1P-1 receptor-mediated biological activity is administered to the subject.

In yet another aspect, the present invention provides a method for treating, preventing or ameliorating an S1P-1 receptor mediated condition in a subject. In such a method, an amount of a modulator of the S1P-1 receptor effective to modulate an S1P-1 receptor-mediated biological activity is administered to the subject. The S1P-1 receptor mediated condition may be, e.g., transplant rejection (solid organ transplant and islet cells); transplant rejection (tissue); cancer; autoimmune/inflammatory diseases; rheumatoid arthritis; lupus; insulin dependent diabetes (Type I); non-insulin dependent diabetes (Type II); multiple sclerosis; psoriasis; ulcerative colitis; inflammatory bowel disease; Crohn's disease; acute and chronic lymphocytic leukemias and lymphomas.

DETAILED DESCRIPTION OF THE INVENTION

The features and other details of the invention will now be more particularly described. It will be understood that particular embodiments described herein are shown by way of illustration and not as limitations of the invention. The principal features of this invention can be employed in various embodiments without departing from the scope of the invention. All parts and percentages are by weight unless otherwise specified.

DEFINITIONS

For convenience, certain terms used in the specification and examples are collected here.

"Treating", includes any effect, e.g., lessening, reducing, modulating, or eliminating, that results in the improvement of the condition, disease, disorder, etc.

"Alkyl" includes saturated aliphatic groups, including straight-chain alkyl groups (e.g., methyl, ethyl, propyl, butyl, pentyl, hexyl, heptyl, octyl, nonyl, decyl), branched-chain alkyl groups (e.g., isopropyl, tert-butyl, isobutyl), cycloalkyl (e.g., alicyclic) groups (e.g., cyclopropyl, cyclopentyl, cyclohexyl, cycloheptyl, cyclooctyl), alkyl substituted cycloalkyl groups, and cycloalkyl substituted alkyl groups. "Alkyl" further includes alkyl groups which have oxygen, nitrogen, sulfur or phosphorous atoms replacing one or more hydrocarbon backbone carbon atoms. In certain embodiments, a straight chain or branched chain alkyl has six or fewer carbon atoms in its backbone (e.g., $C_1$-$C_6$ for straight chain, $C_3$-$C_6$ for branched chain), and more preferably four or fewer. Likewise, preferred cycloalkyls have from three to eight carbon atoms in their ring structure, and more preferably have five or six carbons in the ring structure. "$C_1$-$C_6$" includes alkyl groups containing one to six carbon atoms.

The term "alkyl" also includes both "unsubstituted alkyls" and "substituted alkyls", the latter of which refers to alkyl moieties having substituents replacing a hydrogen on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)). "Alkyl" also includes the side chains of natural and unnatural amino acids.

"Aryl" includes groups with aromaticity, including 5- and 6-membered "unconjugated", or single-ring, aromatic groups that may include from zero to four heteroatoms, as well as "conjugated", or multicyclic, systems with at least one aromatic ring. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions. Representative substituents include the substituents described above, such as halogen, hydroxyl, alkoxy, aryloxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, arylsulfinyl, arylsulfonyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a multicyclic system (e.g., tetralin, methylenedioxyphenyl).

"Alkenyl" includes unsaturated aliphatic groups analogous in length and possible substitution to the alkyls described above, but that contain at least one double bond. For example, the term "alkenyl" includes straight-chain alkenyl groups (e.g., ethenyl, propenyl, butenyl, pentenyl, hexenyl, heptenyl, octenyl, nonenyl, decenyl), branched-chain alkenyl groups, cycloalkenyl (e.g., alicyclic) groups (e.g., cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term "alkenyl" further includes alkenyl groups which include oxygen, nitrogen, sulfur or phosphorous atoms replacing one or more hydrocarbon backbone carbons. In certain embodiments, a straight chain or branched chain alkenyl group has six or fewer carbon atoms in its backbone (e.g., $C_2$-$C_6$ for straight chain, $C_3$-$C_6$ for branched chain.) Likewise, cycloalkenyl groups may have from three to eight carbon atoms in their ring structure, and more preferably have five or six carbons in the ring structure. The term "$C_2$-$C_6$" includes alkenyl groups containing two to six carbon atoms.

The term "alkenyl" also includes both "unsubstituted alkenyls" and "substituted alkenyls", the latter of which refers to alkenyl moieties having substituents replacing a hydrogen on one or more hydrocarbon backbone carbon atoms. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Alkynyl" includes unsaturated aliphatic groups analogous in length and possible substitution to the alkyls described above, but which contain at least one triple bond. For example, "alkynyl" includes straight-chain alkynyl groups (e.g., ethynyl, propynyl, butynyl, pentynyl, hexynyl, heptynyl, octynyl, nonynyl, decynyl), branched-chain alkynyl groups, and cycloalkyl or cycloalkenyl substituted alkynyl groups. The term "alkynyl" further includes alkynyl groups having oxygen, nitrogen, sulfur or phosphorous atoms replacing one or more hydrocarbon backbone carbons. In certain embodiments, a straight chain or branched chain alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms.

The term "alkynyl" also includes both "unsubstituted alkynyls" and "substituted alkynyls", the latter of which refers to alkynyl moieties having substituents replacing a hydrogen on one or more hydrocarbon backbone carbon atoms. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" includes an alkyl group, as defined above, but having from one to ten, more preferably from one to six, carbon atoms in its backbone structure. "Lower alkenyl" and "lower alkynyl" have chain lengths of, for example, 2-5 carbon atoms.

"Acyl" includes compounds and moieties which contain the acyl radical ($CH_3CO$—) or a carbonyl group. "Substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Acylamino" includes moieties wherein an acyl moiety is bonded to an amino group. For example, the term includes alkylcarbonylamino, arylcarbonylamino, carbamoyl and ureido groups.

"Alkoxyalkyl", "alkylaminoalkyl" and "thioalkoxyalkyl" include alkyl groups, as described above, which further include oxygen, nitrogen or sulfur atoms replacing one or more hydrocarbon backbone carbon atoms, e.g., oxygen, nitrogen or sulfur atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, and trichloromethoxy.

The terms "heterocyclyl" or "heterocyclic group" include closed ring structures, e.g., 3- to 10-, or 4- to 7-membered rings, which include one or more heteroatoms. Heterocyclyl groups can be saturated or unsaturated and include pyrrolidine, oxolane, thiolane, piperidine, piperizine, morpholine, lactones, lactams such as azetidinones and pyrrolidinones, sultams, sultones, and the like. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety.

The term "thiocarbonyl" or "thiocarboxy" includes compounds and moieties which contain a carbon connected with a double bond to a sulfur atom.

The term "ether" includes compounds or moieties which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and moieties which contain a sulfur atom bonded to two different carbon or heteroatoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and alkthioalkynyls" refer to compounds or moieties wherein an alkyl, alkenyl, or alkynyl group is bonded to a sulfur atom which is covalently bonded to an alkynyl group.

The term "hydroxy" or "hydroxyl" includes groups with an —OH or —O⁻.

The term "halogen" includes fluorine, bromine, chlorine, iodine, etc. The term "perhalogenated" generally refers to a moiety wherein all hydrogens are replaced by halogen atoms.

"Heteroatom" includes atoms of any element other than carbon or hydrogen. Examples of heteroatoms include nitrogen, oxygen, sulfur and phosphorus.

"At least partially aromatic bicyclic ring system", means a bicyclic ring system where either or both of the rings forming the bicycle are aromatic.

It will be noted that the structure of some of the compounds of the invention includes asymmetric carbon atoms. It is to be understood accordingly that the isomers arising from such asymmetry (e.g., all enantiomers and diastereomers) are included within the scope of the invention, unless indicated otherwise. Such isomers can be obtained in substantially pure form by classical separation techniques and by stereochemically controlled synthesis. Furthermore, the structures and other compounds and moieties discussed in this application also include all tautomers thereof. Alkenes can include either the E- or Z-geometry, where appropriate.

"Combination therapy" (or "co-therapy") includes the administration of a S1P receptor modulator of the invention and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may, but generally is not, intended to encompass the administration of two or more of these therapeutic agents as part of separate monotherapy regimens that incidentally and arbitrarily result in the combinations of the present invention. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical. "Combination therapy" also can embrace the administration of the therapeutic agents as described above in further combination with other biologically active ingredients and non-drug therapies (e.g., surgery or radiation treatment.) Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

An "anionic group," as used herein, refers to a group that is negatively charged at physiological pH. Preferred anionic groups include carboxylate, sulfate, sulfonate, sulfinate, sulfamate, tetrazolyl, phosphate, phosphonate, phosphinate, or phosphorothioate or functional equivalents thereof. "Functional equivalents" of anionic groups are intended to include bioisosteres, e.g., bioisosteres of a carboxylate group. Bioisosteres encompass both classical bioisosteric equivalents and non-classical bioisosteric equivalents. Classical and non-classical bioisosteres are known in the art (see, e.g., Silverman, R. B. *The Organic Chemistry of Drug Design and Drug Action*, Academic Press, Inc.: San Diego, Calif., 1992, pp. 19-23). A particularly preferred anionic group is a carboxylate.

The term "heterocyclic group" is intended to include closed ring structures in which one or more of the atoms in the ring is an element other than carbon, for example, nitrogen, or oxygen or sulfur. Heterocyclic groups can be saturated or unsaturated and heterocyclic groups such as pyrrole and furan can have aromatic character. They include fused ring structures such as quinoline and isoquinoline. Other examples of heterocyclic groups include pyridine and purine. Heterocyclic groups can also be substituted at one or more constituent atoms with, for example, a halogen, a lower alkyl, a lower alkenyl, a lower alkoxy, a lower alkylthio, a lower alkylamino, a lower alkylcarboxyl, a nitro, a hydroxyl, —$CF_3$, —CN, or the like.

An "S1P-modulating agent" includes compound or compositions capable of inducing a detectable change in S1P receptor activity in vivo or in vitro, e.g., at least 10% increase or decrease in S1P activity as measured by a given assay such as the bioassay described hereinbelow.

"$EC_{50}$ of an agent" included that concentration of an agent at which a given activity, including binding of sphingosine or other ligand of an S1P receptor and/or a functional activity of a S1P receptor (e.g., a signaling activity), is 50% maximal for that S1P receptor. Stated differently, the $EC_{50}$ is the concentration of agent that gives 50% activation, when 100% activation is set at the amount of activity of the S1P receptor which does not increase with the addition of more ligand/agonist and 0% activation is set at the amount of activity in the assay in the absence of added ligand/agonist.

"Purified" and like terms relate to the isolation of a molecule or compound in a form that is substantially free of contaminants normally associated with the molecule or compound in a native or natural environment.

An "effective amount" includes an amount sufficient to produce a selected effect. For example, an effective amount of an S1P receptor antagonist is an amount that decreases the cell signaling activity of the S1P receptor.

"Immunomodulation" includes effects on the functioning of the immune system, and includes both the enhancement of an immune response as well as suppression of the immune response.

The compounds of the invention and the other pharmacologically active agent may be administered to a patient simultaneously, sequentially or in combination. It will be appreciated that when using a combination of the invention, the compound of the invention and the other pharmacologically active agent may be in the same pharmaceutically acceptable carrier and therefore administered simultaneously. They may be in separate pharmaceutical carriers such as conventional oral dosage forms which are taken simultaneously. The term "combination" further refers to the case where the compounds are provided in separate dosage forms and are administered sequentially.

The compounds of the invention may be administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician.

An appropriate dosage level will generally be about 0.001 to 50 mg per kg patient body weight per day, which may be administered in single or multiple doses. Preferably, the dosage level will be about 0.01 to about 25 mg/kg per day; more preferably about 0.05 to about 10 mg/kg per day. For example, in the treatment or prevention of a disorder of the central nervous system, a suitable dosage level is about 0.001 to 10 mg/kg per day, preferably about 0.005 to 5 mg/kg per day, and especially about 0.01 to 1 mg/kg per day. The compounds may be administered on a regimen of 1 to 4 times per day, preferably once or twice per day.

It will be appreciated that the amount of the compound of the invention required for use in any treatment will vary not only with the particular compounds or composition selected but also with the route of administration, the nature of the condition being treated, and the age and condition of the patient, and will ultimately be at the discretion of the attendant physician.

The compositions and combination therapies of the invention may be administered in combination with a variety of pharmaceutical excipients, including stabilizing agents, carriers and/or encapsulation formulations as described herein.

Aqueous compositions of the present invention comprise an effective amount of the compounds of the invention, dissolved or dispersed in a pharmaceutically acceptable carrier or aqueous medium.

"Pharmaceutically or pharmacologically acceptable" include molecular entities and compositions that do not produce an adverse, allergic or other untoward reaction when administered to an animal, or a human, as appropriate. "Pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For human administration, preparations should meet sterility, pyrogenicity, general safety and purity standards as required by FDA Office of Biologics standards.

The compositions and combination therapies of the invention will then generally be formulated for parenteral administration, e.g., formulated for injection via the intravenous, intramuscular, subcutaneous, intralesional, or even intraperitoneal routes. The preparation of an aqueous composition that contains a composition of the invention or an active component or ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Solutions of active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

Therapeutic or pharmacological compositions of the present invention will generally comprise an effective amount of the component(s) of the combination therapy, dissolved or dispersed in a pharmaceutically acceptable medium. Pharmaceutically acceptable media or carriers include any and all solvents, dispersion media, coatings, antibacterial and antifungal agents, isotonic and absorption delaying agents and the like. The use of such media and agents for pharmaceutical active substances is well known in the art. Supplementary active ingredients can also be incorporated into the therapeutic compositions of the present invention.

The preparation of pharmaceutical or pharmacological compositions will be known to those of skill in the art in light of the present disclosure. Typically, such compositions may be prepared as injectables, either as liquid solutions or suspensions; solid forms suitable for solution in, or suspension in, liquid prior to injection; as tablets or other solids for oral administration; as time release capsules; or in any other form currently used, including cremes, lotions, mouthwashes, inhalants and the like.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly, concentrated solutions for intramuscular injection is also contemplated. In this regard, the use of DMSO as solvent is preferred as this will result in extremely rapid penetration, delivering high concentrations of the active compound(s) or agent(s) to a small area.

The use of sterile formulations, such as saline-based washes, by surgeons, physicians or health care workers to cleanse a particular area in the operating field may also be particularly useful. Therapeutic formulations in accordance with the present invention may also be reconstituted in the form of mouthwashes, or in conjunction with antifungal reagents. Inhalant forms are also envisioned. The therapeutic formulations of the invention may also be prepared in forms suitable for topical administration, such as in cremes and lotions.

Suitable preservatives for use in such a solution include benzalkonium chloride, benzethonium chloride, chlorobutanol, thimerosal and the like. Suitable buffers include boric acid, sodium and potassium bicarbonate, sodium and potassium borates, sodium and potassium carbonate, sodium acetate, sodium biphosphate and the like, in amounts sufficient to maintain the pH at between about pH 6 and pH 8, and preferably, between about pH 7 and pH 7.5. Suitable tonicity agents are dextran 40, dextran 70, dextrose, glycerin, potassium chloride, propylene glycol, sodium chloride, and the like, such that the sodium chloride equivalent of the ophthalmic solution is in the range 0.9 plus or minus 0.2%. Suitable antioxidants and stabilizers include sodium bisulfite, sodium metabisulfite, sodium thiosulfite, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose and the like.

Upon formulation, therapeutics will be administered in a manner compatible with the dosage formulation, and in such amount as is pharmacologically effective. The formulations are easily administered in a variety of dosage forms, such as the type of injectable solutions described above, but drug release capsules and the like can also be employed.

In this context, the quantity of active ingredient and volume of composition to be administered depends on the host animal to be treated. Precise amounts of active compound required for administration depend on the judgment of the practitioner and are peculiar to each individual.

A minimal volume of a composition required to disperse the active compounds is typically utilized. Suitable regimes for administration are also variable, but would be typified by initially administering the compound and monitoring the results and then giving further controlled doses at further intervals. For example, for parenteral administration, a suitably buffered, and if necessary, isotonic aqueous solution would be prepared and used for intravenous, intramuscular, subcutaneous or even intraperitoneal administration. One dosage could be dissolved in 1 ml of isotonic NaCl solution and either added to 1000 ml of hypodermolysis fluid or injected at the proposed site of infusion, (see for example, *Remington's Pharmaceutical Sciences* 15th Edition, pages 1035-1038 and 1570-1580).

In certain embodiments, active compounds may be administered orally. This is contemplated for agents which are generally resistant, or have been rendered resistant, to proteolysis by digestive enzymes. Such compounds are contemplated to include chemically designed or modified agents; dextrorotatory peptides; and peptide and liposomal formulations in time release capsules to avoid peptidase and lipase degradation.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze drying techniques which yield a powder of the active ingredient plus any additional desired ingredient from a previously sterile-filtered solution thereof.

The preparation of more, or highly, concentrated solutions for direct injection is also contemplated, where the use of DMSO as solvent is envisioned to result in extremely rapid penetration, delivering high concentrations of the active agents to a small area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure.

In addition to the compounds formulated for parenteral administration, such as intravenous or intramuscular injection, other pharmaceutically acceptable forms include, e.g., tablets or other solids for oral administration; liposomal formulations; time-release capsules; and any other form currently used, including cremes.

Additional formulations suitable for other modes of administration include suppositories. For suppositories, traditional binders and carriers may include, for example, polyalkylene glycols or triglycerides; such suppositories may be formed from mixtures containing the active ingredient in the range of 0.5% to 10%, preferably 1%-2%.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders.

In certain defined embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor.

The pharmaceutical compositions of this invention may be used in the form of a pharmaceutical preparation, for example, in solid, semisolid or liquid form, which contains one or more of the compound of the invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active object compound is included in the pharmaceutical composition in an amount sufficient to produce the desired effect upon the process or condition of the disease.

For preparing solid compositions such as tablets, the principal active ingredient is mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compositions of the invention may be incorporated for administration orally or by injection include aqueous solution, suitably flavored syrups, aqueous or oil suspensions, and emulsions with acceptable oils such as cottonseed oil, sesame oil, coconut oil or peanut oil, or with a solubilizing or emulsifying agent suitable for intravenous use, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulized by use of inert gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

For treating clinical conditions and diseases noted above, the compound of this invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

The present invention relates, in one embodiment, to compounds according to Formula I. Desirably, p and q are 0 or 1; Z is $CH_2$, O, S or a direct bond; n is 0 or 1; $R^2$ is methyl; and $R^3$ and $R^4$ are independently hydrogen or methyl.

Desirably, $R^1$ is $C_{1-5}$ alkyl, $C_{1-5}$ alkoxyl, trifluoromethyl, phenyl or phenyl substituted by $C_{1-5}$ alkyl, halogen, trifluoromethyl or cyano.

X is desirably COOH, $P(O)(OH)_2$ or 1H-tetrazol-5-yl. X may alternately be combined with Y, to form, e.g,:

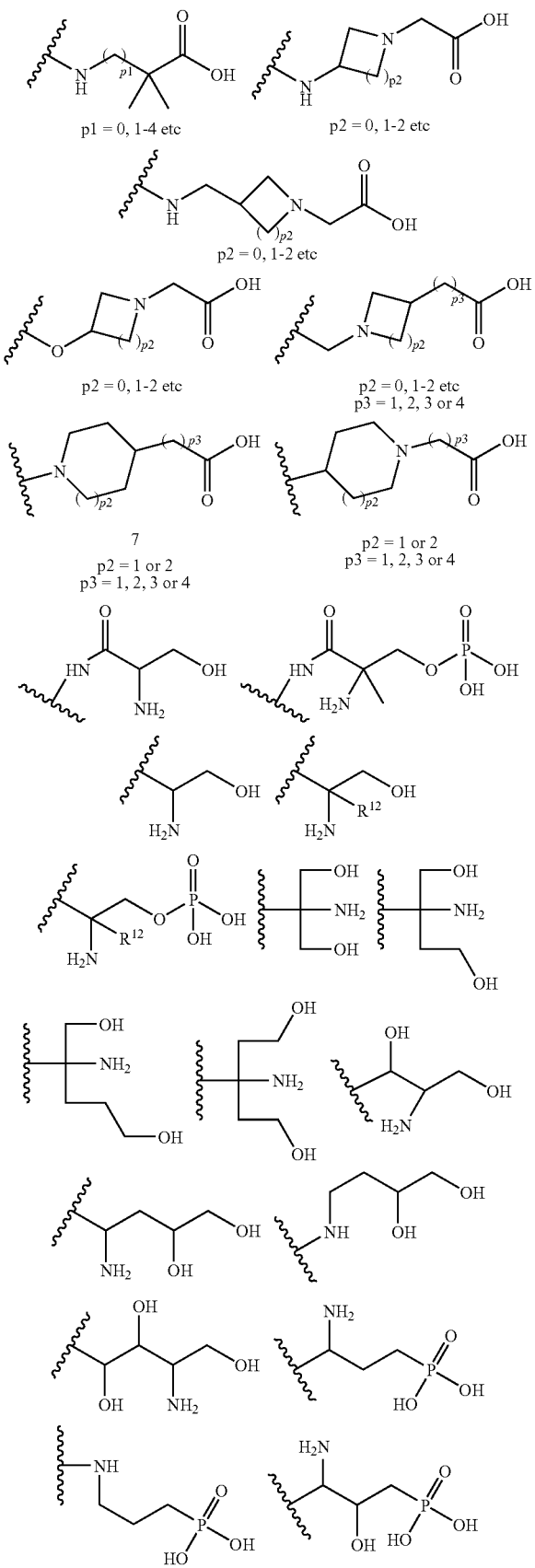

17

-continued

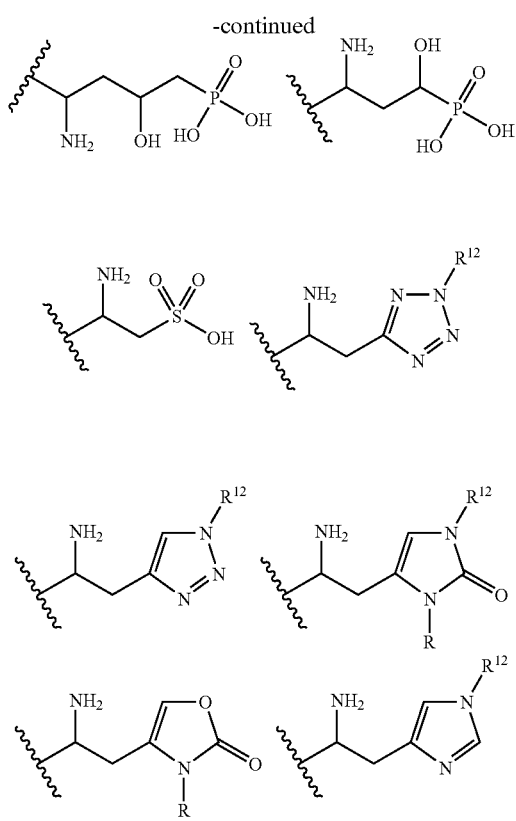

A is desirably substituted or unsubstituted aryl or heteroaryl, e.g. wherein $R^{11}$ is hydrogen or $C_{1-6}$ alkyl; and the left and right asterisks indicate the point of attachment in formula (I);

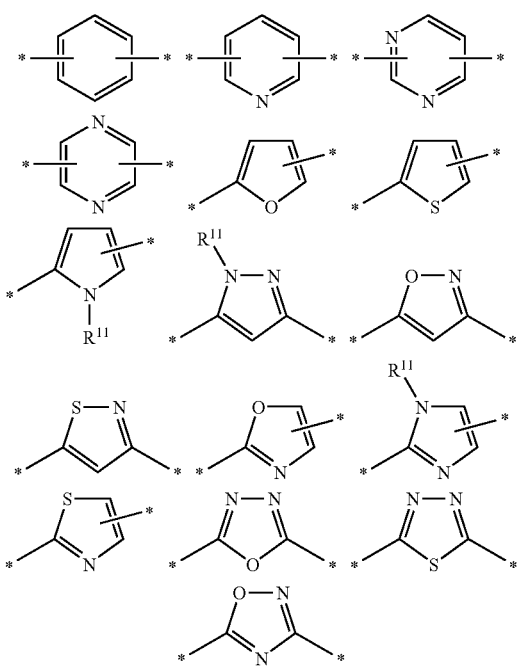

18

B is desirably a cyclic urea, e.g.,

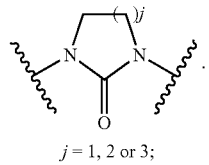

$j = 1, 2$ or 3;

In certain embodiments, the present invention relates to a compound represented by formula II:

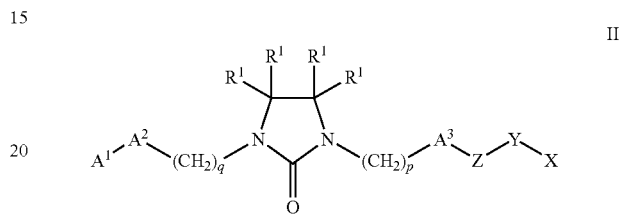

or a pharmaceutically acceptable salt thereof, wherein, $A^1$ is H, $C_{1-8}$ alkyl, cycloalkyl, haloalkyl, aryl, aralkyl, —$OR^2$, —$SR^2$, —$S(O)R^2$, —$S(O)_2R^2$; —$C(O)R^2$, —$CO_2R^2$; or —$C(R^3)_2R^2$;

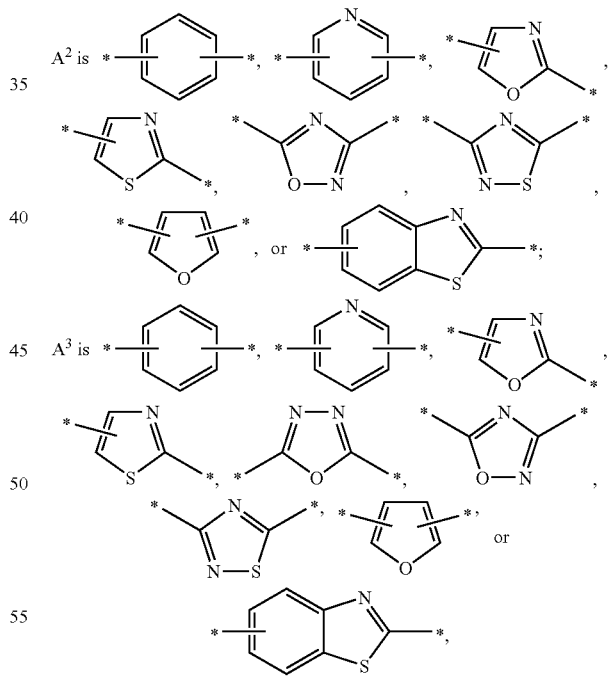

each of which may optionally be substituted with a halogen, trifluoromethyl, or alkoxy;
p and q represent independently 0, 1, 2, 3 or 4;
Z is $(CR^3R^4)_n$, C(O), or a direct bond;
n is 1, 2, 3 or 4;
$R^1$ is H or $C_{1-6}$ alkyl;
$R^2$ is alkyl, aryl, heteroaryl, or aralkyl;

R³ and R⁴ represent independently for each occurrence hydrogen, halo, hydroxyl, $C_{1-6}$ alkyl, $C_{1-5}$ alkoxy, aryl, or heteroaryl;

X is $WC(O)OR^5$ or $WS(O)_2NH_2$;

R⁵ is hydrogen or $C_{1-4}$ alkyl;

W is a direct bond, oxygen or $C_{1-4}$ alkylene;

Y is a bond or

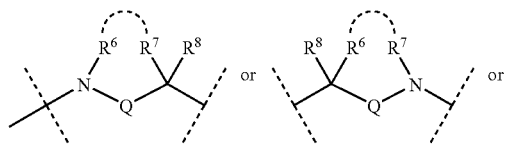

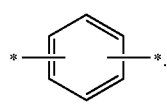

Q is a direct bond, C=O or $(CR^9R^{10})_m$;

m is 1, 2 or 3;

R⁶ and R⁷ each represent independently hydrogen, halo, hydroxyl, $C_{1-6}$ alkyl, or $C_{1-5}$ alkoxy; or R⁶ and R⁷ may be joined together with the atoms to which they are attached to form a 4- to 7-membered ring;

R⁸ is hydrogen, halogen, hydroxyl, amino, $C_{1-6}$ alkyl, or $C_{1-5}$ alkoxy; and R⁹ and R¹⁰ each independently represent hydrogen, halo, $C_{1-6}$ alkyl, or $-CO_2R^5$.

In certain embodiments, the present invention relates to the aforementioned compound, wherein A¹ is H, $C_{1-8}$ alkyl, cycloalkyl, haloalkyl, aryl, or aralkyl.

In certain embodiments, the present invention relates to the aforementioned compound, wherein A² is

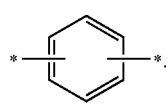

In certain embodiments, the present invention relates to the aforementioned compound, wherein A³ is

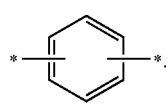

In certain embodiments, the present invention relates to the aforementioned compound, wherein X is $WC(O)OR^5$.

In certain embodiments, the present invention relates to the aforementioned compound, wherein X is $WCO_2H$.

In certain embodiments, the present invention relates to the aforementioned compound, wherein Y is

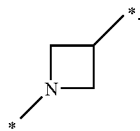

In certain embodiments, the present invention relates to the aforementioned compound, wherein A² is

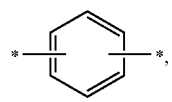

and A³ is

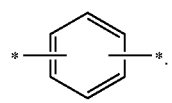

In certain embodiments, the present invention relates to the aforementioned compound, wherein A² is

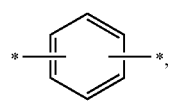

A³ is

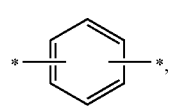

and Y is

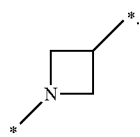

In certain embodiments, the present invention relates to the aforementioned compound, wherein A² is

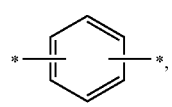

$A^3$ is

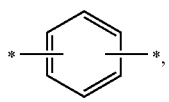

and X is $WCO_2H$.

In certain instances, the invention features a compound selected from the group consisting of

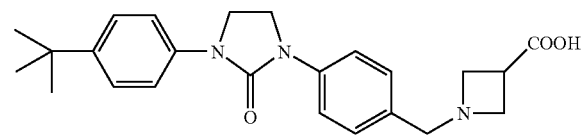

having the chemical name 1-(4-(3-(4-tert-butylphenyl)-2-oxoimidazolidin-1-yl)benzyl)azetidine-3-carboxylic acid,

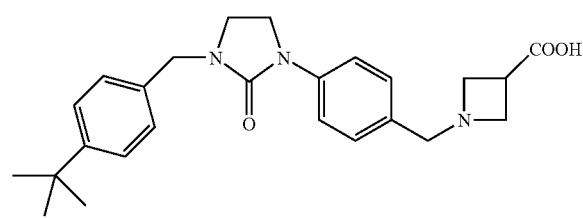

having the chemical name 1-(4-(3-(4-tert-butylbenzyl)-2-oxoimidazolidin-1-yl)benzyl)azetidine-3-carboxylic acid,

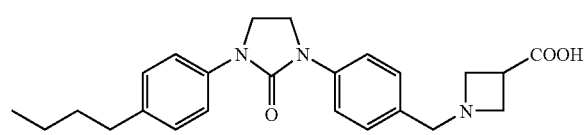

having the chemical name 1-(4-(3-(4-butylphenyl)-2-oxoimidazolidin-1-yl)benzyl)azetidine-3-carboxylic acid,

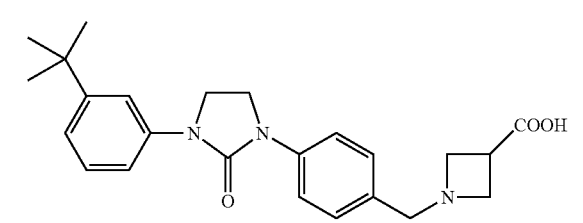

having the chemical name 1-(4-(3-(3-tert-butylphenyl)-2-oxoimidazolidin-1-yl)benzyl)azetidine-3-carboxylic acid,

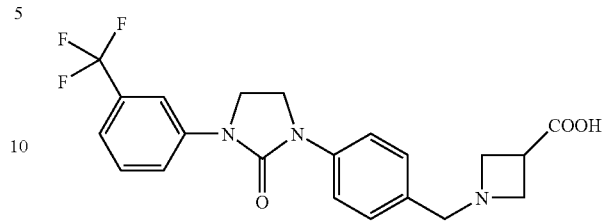

having the chemical name 1-(4-(2-oxo-3-(3-(trifluoromethyl)phenyl)imidazolidin-1-yl)benzyl)azetidine-3-carboxylic acid,

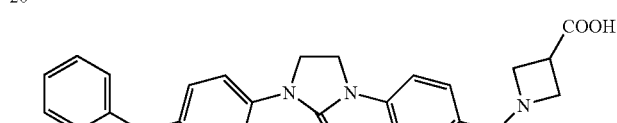

having the chemical name 1-(4-(3-(4-benzylphenyl)-2-oxoimidazolidin-1-yl)benzyl)azetidine-3-carboxylic acid,

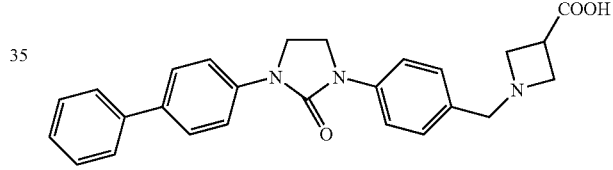

having the chemical name 1-(4-(3-(biphenyl-4-yl)-2-oxoimidazolidin-1-yl)benzyl)azetidine-3-carboxylic acid,

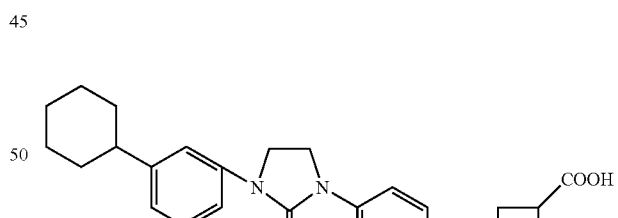

having the chemical name 1-(4-(3-(3-cyclohexylphenyl)-2-oxoimidazolidin-1-yl)benzyl)azetidine-3-carboxylic acid,

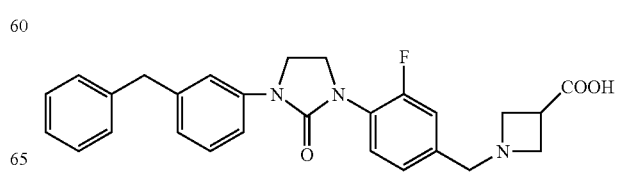

having the chemical name 1-(4-(3-(3-benzylphenyl)-2-ox-oimidazolidin-1-yl)-3-fluorobenzyl)azetidine-3-carboxylic acid,

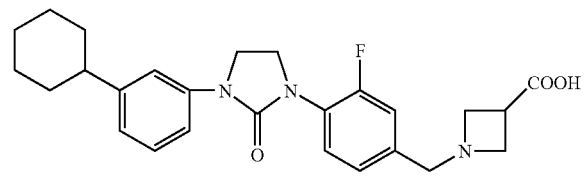

having the chemical name 1-(4-(3-(3-cyclohexylphenyl)-2-oxoimidazolidin-1-yl)-3-fluorobenzyl)azetidine-3-carboxylic acid,

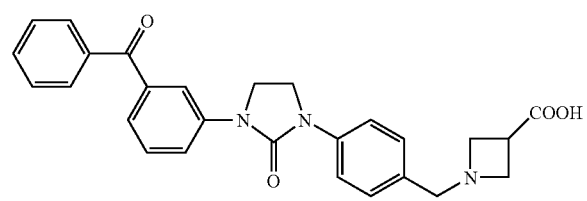

having the chemical name 1-(4-(3-(3-benzoylphenyl)-2-ox-oimidazolidin-1-yl)benzyl)azetidine-3-carboxylic acid,

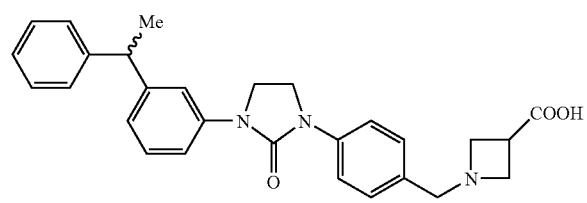

having the chemical name 1-(4-(2-oxo-3-(3-(1-phenylethyl)phenyl)imidazolidin-1-yl)benzyl)azetidine-3-carboxylic acid,

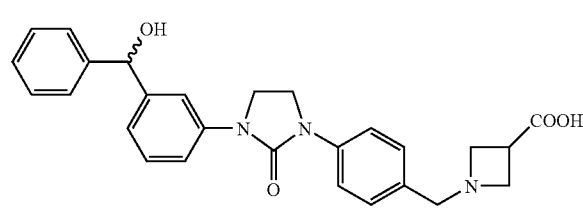

having the chemical name 1-(4-(3-(3-(hydroxy(phenyl)methyl)phenyl)-2-oxoimidazolidin-1-yl)benzyl)azetidine-3-carboxylic acid,

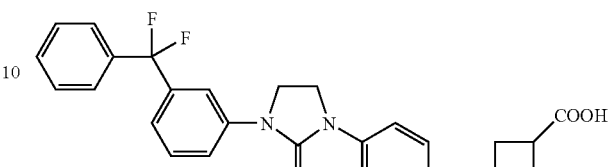

having the chemical name 1-(4-(3-(3-(difluoro(phenyl)methyl)phenyl)-2-oxoimidazolidin-1-yl)benzyl)azetidine-3-carboxylic acid,

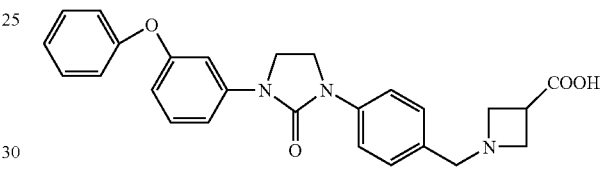

having the chemical name 1-(4-(2-oxo-3-(3-phenoxyphenyl)imidazolidin-1-yl)benzyl)azetidine-3-carboxylic acid,

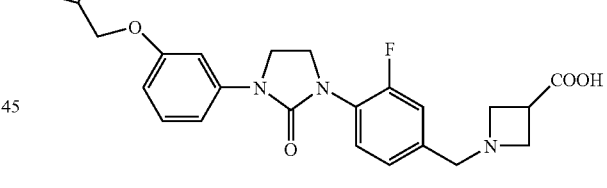

having the chemical name 1-(4-(3-(3-(cyclobutylmethoxy)phenyl)-2-oxoimidazolidin-1-yl)-3-fluorobenzyl)azetidine-3-carboxylic acid,

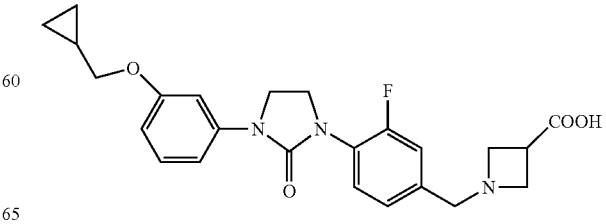

having the chemical name 1-(4-(3-(3-(cyclopropylmethoxy) phenyl)-2-oxoimidazolidin-1-yl)-3-fluorobenzyl)azetidine-3-carboxylic acid,

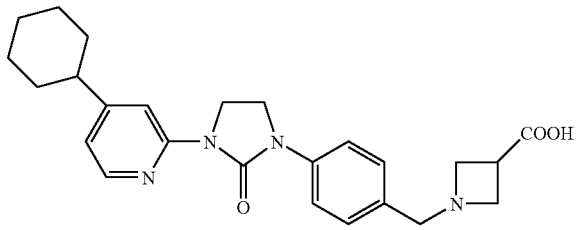

having the chemical name 1-(4-(3-(4-cyclohexylpyridin-2-yl)-2-oxoimidazolidin-1-yl)benzyl)azetidine-3-carboxylic acid,

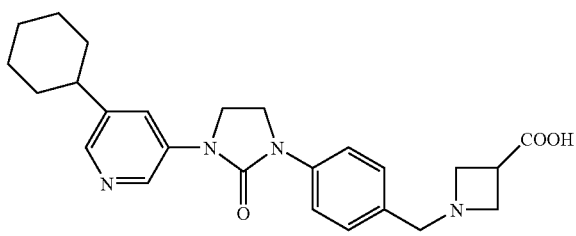

having the chemical name 1-(4-(3-(5-cyclohexylpyridin-3-yl)-2-oxoimidazolidin-1-yl)benzyl)azetidine-3-carboxylic acid,

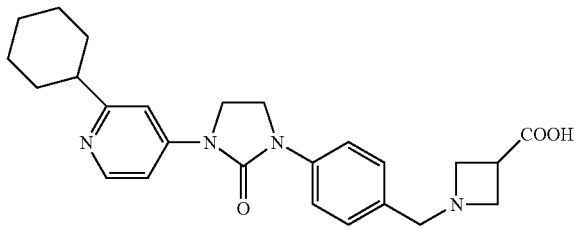

having the chemical name 1-(4-(3-(2-cyclohexylpyridin-4-yl)-2-oxoimidazolidin-1-yl)benzyl)azetidine-3-carboxylic acid,

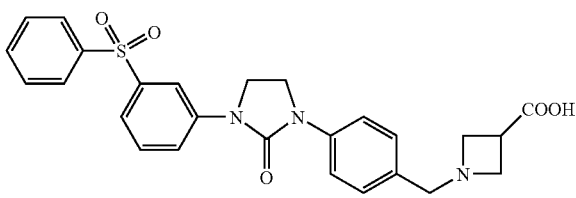

having the chemical name 1-(4-(2-oxo-3-(3-(phenylsulfonyl) phenyl)imidazolidin-1-yl)benzyl)azetidine-3-carboxylic acid,

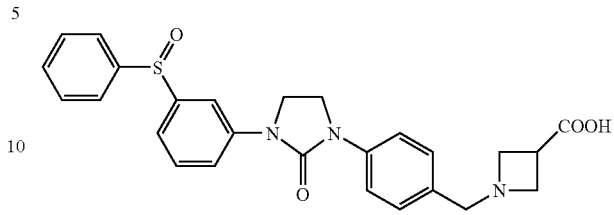

having the chemical name 1-(4-(2-oxo-3-(3-(phenylsulfinyl) phenyl)imidazolidin-1-yl)benzyl)azetidine-3-carboxylic acid,

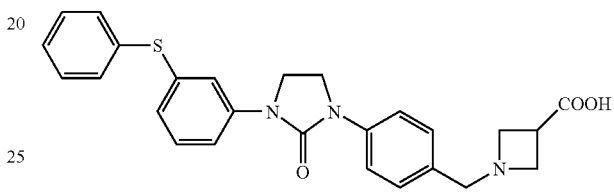

having the chemical name 1-(4-(2-oxo-3-(3-(phenylthio)phenyl)imidazolidin-1-yl)benzyl)azetidine-3-carboxylic acid,

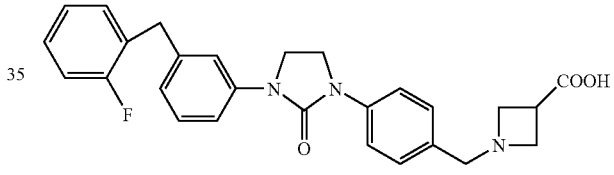

having the chemical name 1-(4-(3-(3-(2-fluorobenzyl)phenyl)-2-oxoimidazolidin-1-yl)benzyl)azetidine-3-carboxylic acid,

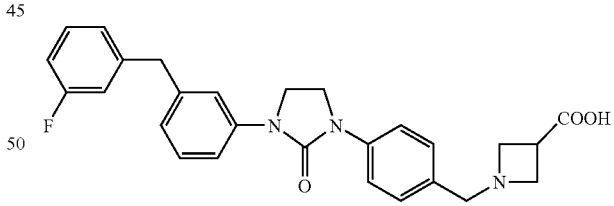

having the chemical name 1-(4-(3-(3-(3-fluorobenzyl)phenyl)-2-oxoimidazolidin-1-yl)benzyl)azetidine-3-carboxylic acid,

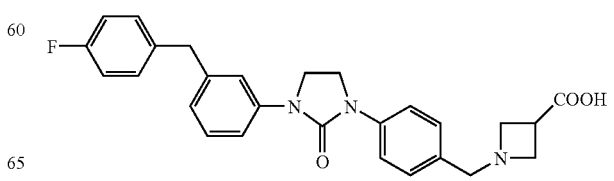

having the chemical name 1-(4-(3-(3-(4-fluorobenzyl)phenyl)-2-oxoimidazolidin-1-yl)benzyl)azetidine-3-carboxylic acid,

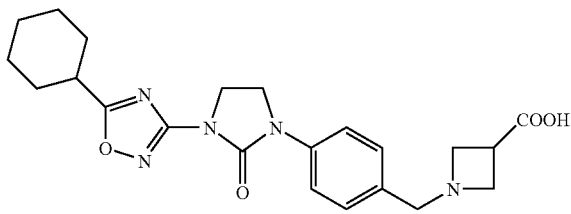

having the chemical name 1-(4-(3-(5-cyclohexyl-1,2,4-oxadiazol-3-yl)-2-oxoimidazolidin-1-yl)benzyl)azetidine-3-carboxylic acid,

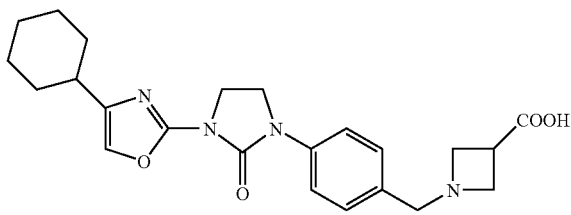

having the chemical name 1-(4-(3-(4-cyclohexyloxazol-2-yl)-2-oxoimidazolidin-1-yl)benzyl)azetidine-3-carboxylic acid,

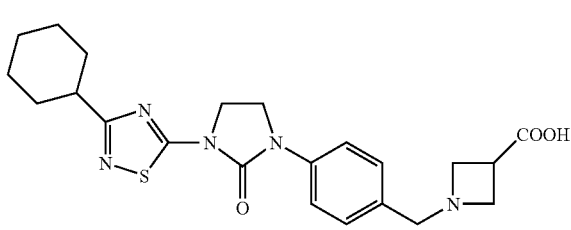

having the chemical name 1-(4-(3-(3-cyclohexyl-1,2,4-thiadiazol-5-yl)-2-oxoimidazolidin-1-yl)benzyl)azetidine-3-carboxylic acid,

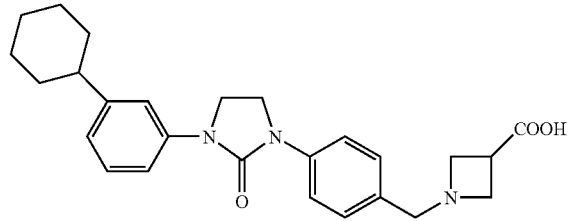

having the chemical name 1-(4-(3-(3-cyclohexylphenyl)-2-oxoimidazolidin-1-yl)benzyl)azetidine-3-carboxylic acid,

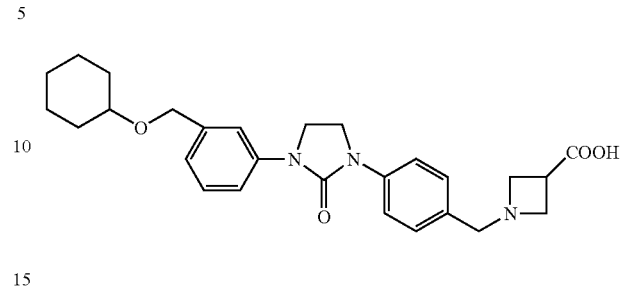

having the chemical name 1-(4-(3-(3-(cyclohexyloxymethyl)phenyl)-2-oxoimidazolidin-1-yl)benzyl)azetidine-3-carboxylic acid,

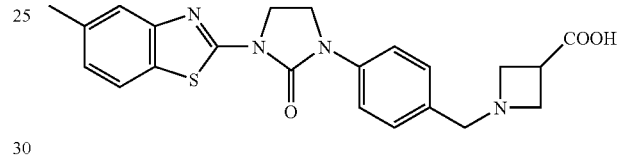

having the chemical name 1-(4-(3-(5-methylbenzo[d]thiazol-2-yl)-2-oxoimidazolidin-1-yl)benzyl)azetidine-3-carboxylic acid,

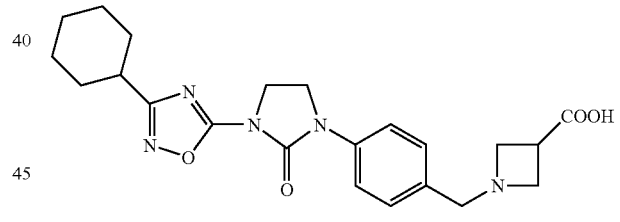

having the chemical name 1-(4-(3-(3-cyclohexyl-1,2,4-oxadiazol-5-yl)-2-oxoimidazolidin-1-yl)benzyl)azetidine-3-carboxylic acid,

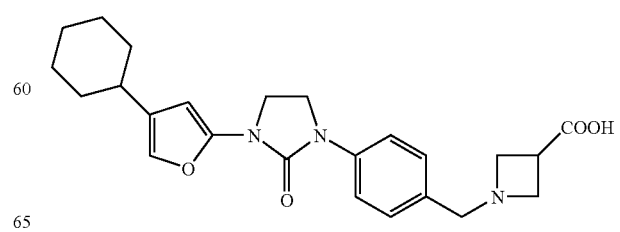

having the chemical name 1-(4-(3-(4-cyclohexylfuran-2-yl)-2-oxoimidazolidin-1-yl)benzyl)azetidine-3-carboxylic acid,

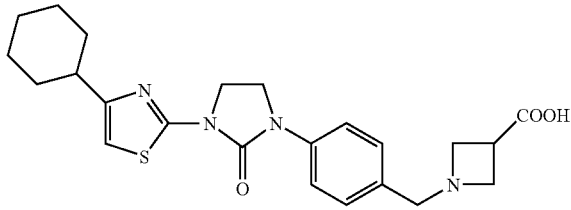

having the chemical name 1-(4-(3-(4-cyclohexylthiazol-2-yl)-2-oxoimidazolidin-1-yl)benzyl)azetidine-3-carboxylic acid,

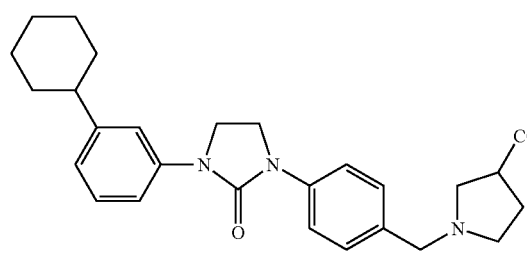

having the chemical name 1-(4-(3-(3-cyclohexylphenyl)-2-oxoimidazolidin-1-yl)benzyl)pyrrolidine-3-carboxylic acid,

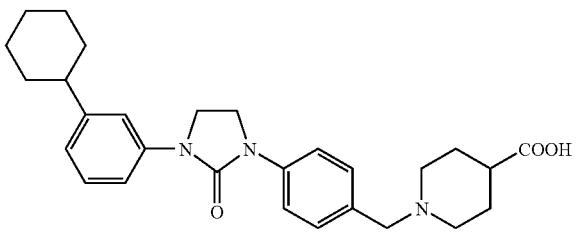

having the chemical name 1-(4-(3-(3-cyclohexylphenyl)-2-oxoimidazolidin-1-yl)benzyl)piperidine-4-carboxylic acid,

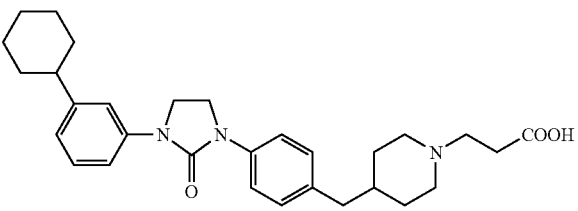

having the chemical name 3-(4-(4-(3-(3-cyclohexylphenyl)-2-oxoimidazolidin-1-yl)benzyl)piperidin-1-yl)propanoic acid,

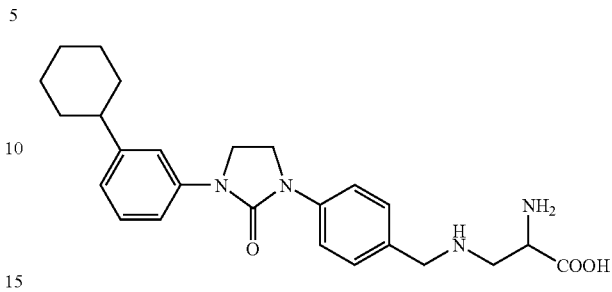

having the chemical name 2-amino-3-(4-(3-(3-cyclohexylphenyl)-2-oxoimidazolidin-1-yl)benzylamino)propanoic acid,

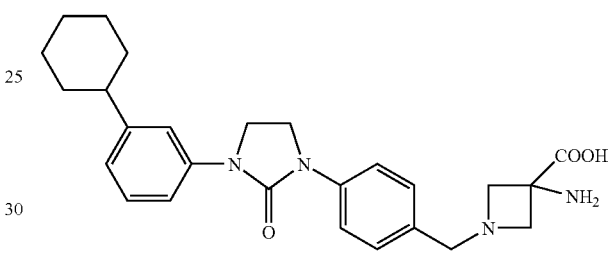

having the chemical name 3-amino-1-(4-(3-(3-cyclohexylphenyl)-2-oxoimidazolidin-1-yl)benzyl)azetidine-3-carboxylic acid,

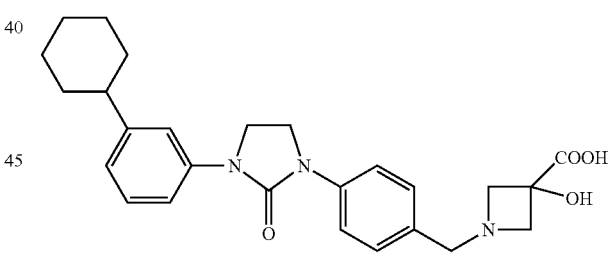

having the chemical name 1-(4-(3-(3-cyclohexylphenyl)-2-oxoimidazolidin-1-yl)benzyl)-3-hydroxyazetidine-3-carboxylic acid,

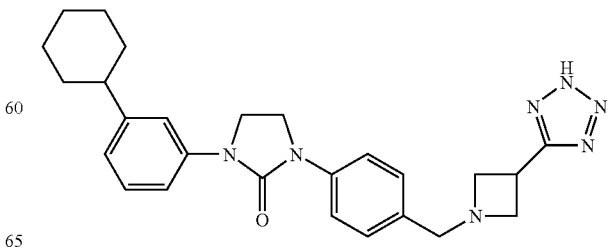

having the chemical name 1-(4-((3-(2H-tetrazol-5-yl)azetidin-1-yl)methyl)phenyl)-3-(3-cyclohexylphenyl)imidazolidin-2-one,

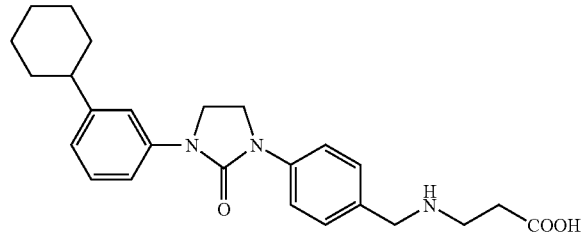

having the chemical name 3-(4-(3-(3-cyclohexylphenyl)-2-oxoimidazolidin-1-yl)benzylamino)propanoic acid,

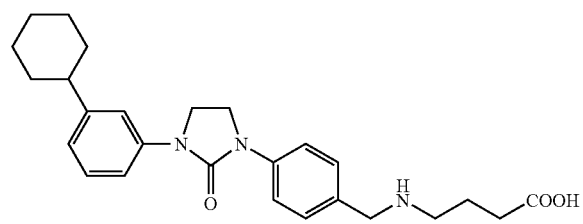

having the chemical name 4-(4-(3-(3-cyclohexylphenyl)-2-oxoimidazolidin-1-yl)benzylamino)butanoic acid,

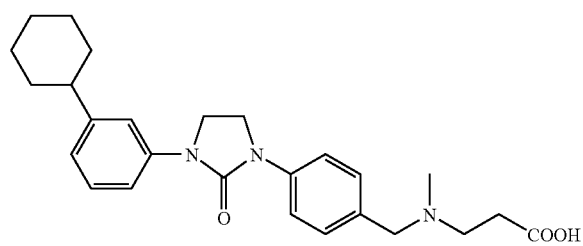

having the chemical name 3-((4-(3-(3-cyclohexylphenyl)-2-oxoimidazolidin-1-yl)benzyl)(methyl)amino)propanoic acid,

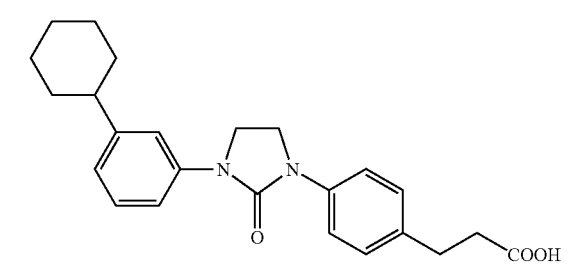

having the chemical name 3-(4-(3-(3-cyclohexylphenyl)-2-oxoimidazolidin-1-yl)phenyl)propanoic acid,

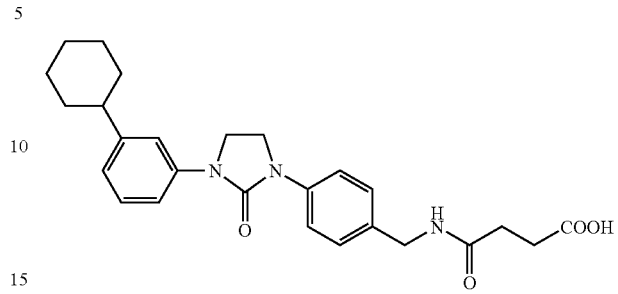

having the chemical name 4-(4-(3-(3-cyclohexylphenyl)-2-oxoimidazolidin-1-yl)benzylamino)-4-oxobutanoic acid,

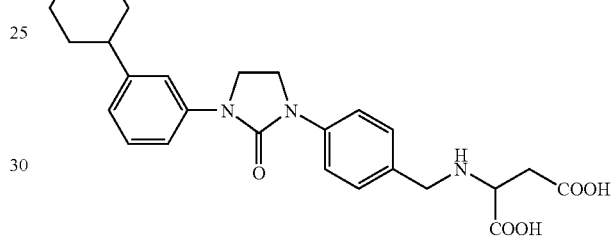

having the chemical name 2-(4-(3-(3-cyclohexylphenyl)-2-oxoimidazolidin-1-yl)benzylamino)succinic acid,

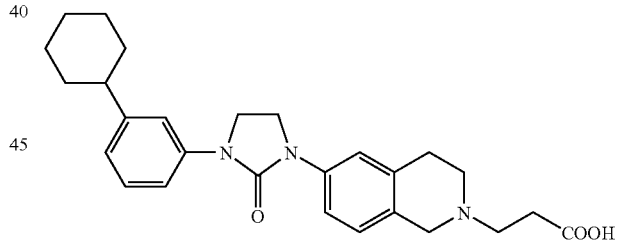

having the chemical name 3-(6-(3-(3-cyclohexylphenyl)-2-oxoimidazolidin-1-yl)-3,4-dihydroisoquinolin-2(1H)-yl)propanoic acid,

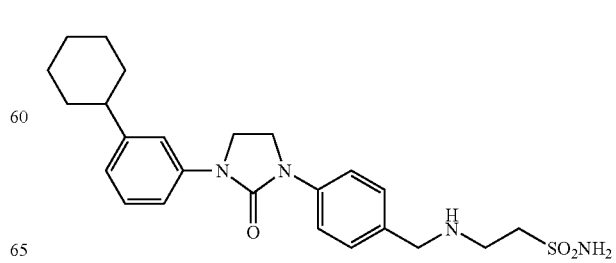

having the chemical name 2-(4-(3-(3-cyclohexylphenyl)-2-oxoimidazolidin-1-yl)benzylamino)ethanesulfonamide,

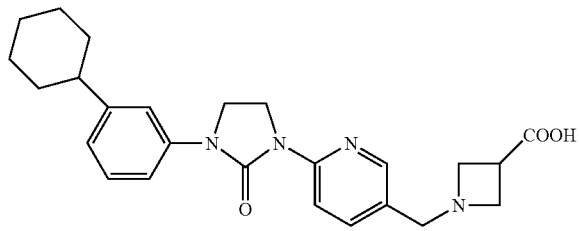

having the chemical name 1-((6-(3-(3-cyclohexylphenyl)-2-oxoimidazolidin-1-yl)pyridin-3-yl)methyl)azetidine-3-carboxylic acid,

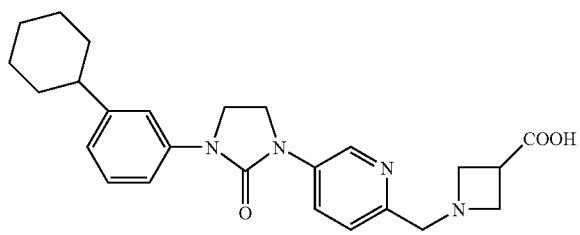

having the chemical name 1-((5-(3-(3-cyclohexylphenyl)-2-oxoimidazolidin-1-yl)pyridin-2-yl)methyl)azetidine-3-carboxylic acid,

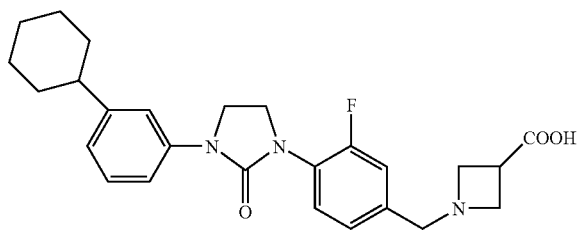

having the chemical name 1-(4-(3-(3-cyclohexylphenyl)-2-oxoimidazolidin-1-yl)-3-fluorobenzyl)azetidine-3-carboxylic acid,

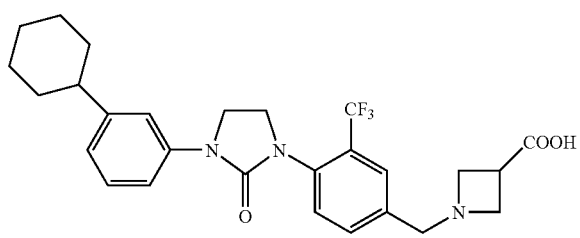

having the chemical name 1-(4-(3-(3-cyclohexylphenyl)-2-oxoimidazolidin-1-yl)-3-(trifluoromethyl)benzyl)azetidine-3-carboxylic acid,

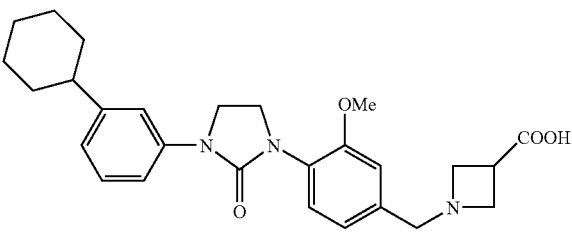

having the chemical name 1-(4-(3-(3-cyclohexylphenyl)-2-oxoimidazolidin-1-yl)-3-methoxybenzyl)azetidine-3-carboxylic acid,

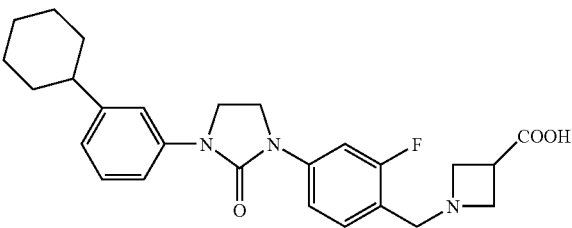

having the chemical name 1-(4-(3-(3-cyclohexylphenyl)-2-oxoimidazolidin-1-yl)-2-fluorobenzyl)azetidine-3-carboxylic acid,

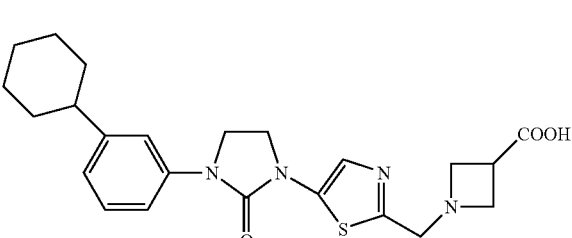

having the chemical name 1-((5-(3-(3-cyclohexylphenyl)-2-oxoimidazolidin-1-yl)thiazol-2-yl)methyl)azetidine-3-carboxylic acid,

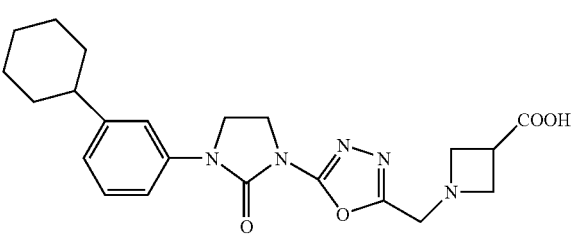

having the chemical name 1-((5-(3-(3-cyclohexylphenyl)-2-oxoimidazolidin-1-yl)-1,3,4-oxadiazol-2-yl)methyl)azetidine-3-carboxylic acid,

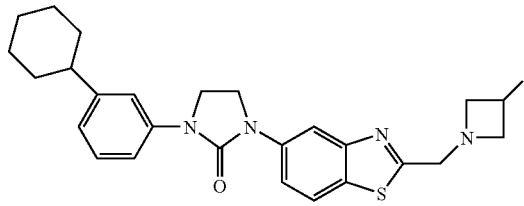

having the chemical name 1-((5-(3-(3-cyclohexylphenyl)-2-oxoimidazolidin-1-yl)benzo[d]thiazol-2-yl)methyl)azetidine-3-carboxylic acid,

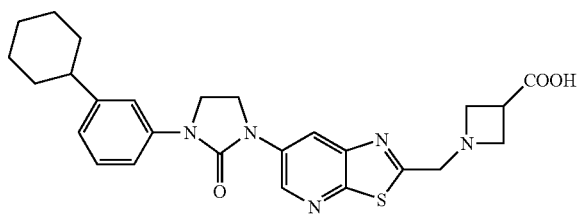

having the chemical name 1-((6-(3-(3-cyclohexylphenyl)-2-oxoimidazolidin-1-yl)thiazolo[5,4-b]pyridin-2-yl)methyl)azetidine-3-carboxylic acid,

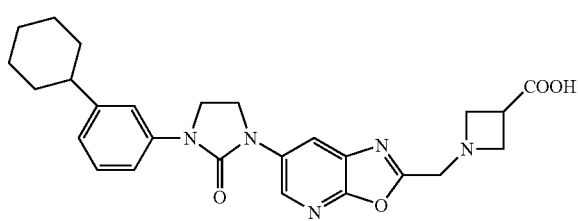

having the chemical name 1-((6-(3-(3-cyclohexylphenyl)-2-oxoimidazolidin-1-yl)oxazolo[5,4-b]pyridin-2-yl)methyl)azetidine-3-carboxylic acid,

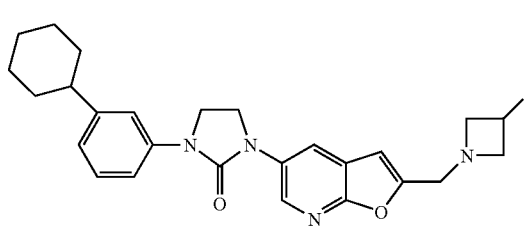

having the chemical name 1-((5-(3-(3-cyclohexylphenyl)-2-oxoimidazolidin-1-yl)furo[2,3-b]pyridin-2-yl)methyl)azetidine-3-carboxylic acid,

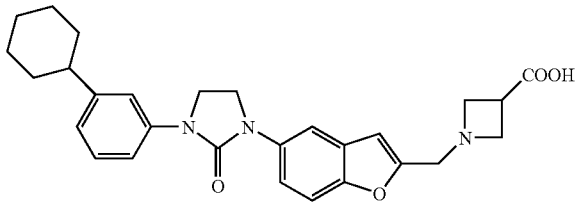

having the chemical name 1-((5-(3-(3-cyclohexylphenyl)-2-oxoimidazolidin-1-yl)benzofuran-2-yl)methyl)azetidine-3-carboxylic acid,

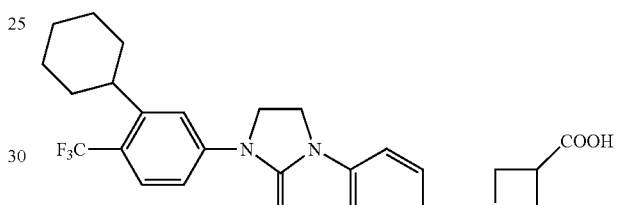

having the chemical name 1-(4-(3-(3-cyclohexyl-4-(trifluoromethyl)phenyl)-2-oxoimidazolidin-1-yl)benzyl)azetidine-3-carboxylic acid,

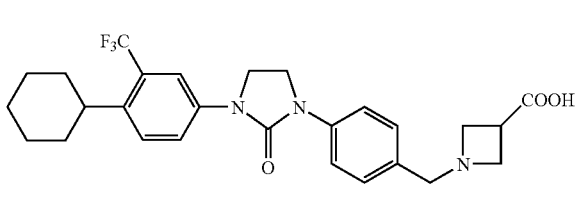

having the chemical name 1-(4-(3-(4-cyclohexyl-3-(trifluoromethyl)phenyl)-2-oxoimidazolidin-1-yl)benzyl)azetidine-3-carboxylic acid,

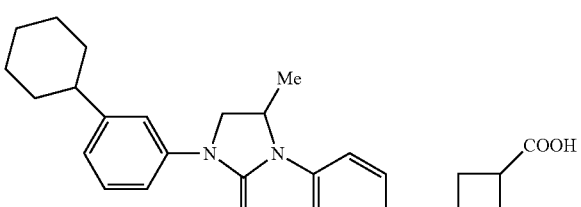

having the chemical name 1-(4-(3-(3-cyclohexylphenyl)-5-methyl-2-oxoimidazolidin-1-yl)benzyl)azetidine-3-carboxylic acid,

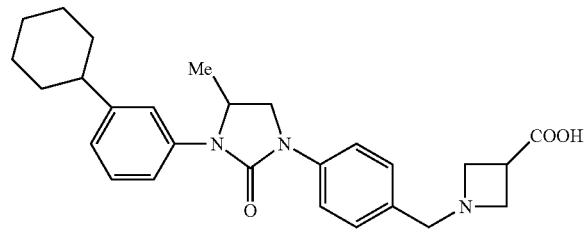

having the chemical name 1-(4-(3-(3-cyclohexylphenyl)-4-methyl-2-oxoimidazolidin-1-yl)benzyl)azetidine-3-carboxylic acid,

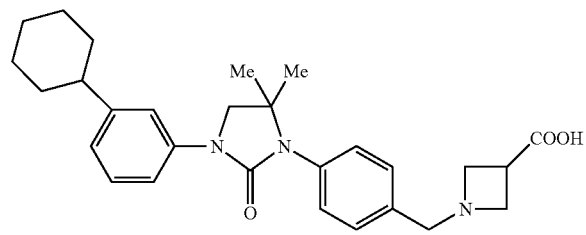

having the chemical name 1-(4-(3-(3-cyclohexylphenyl)-5,5-dimethyl-2-oxoimidazolidin-1-yl)benzyl)azetidine-3-carboxylic acid,

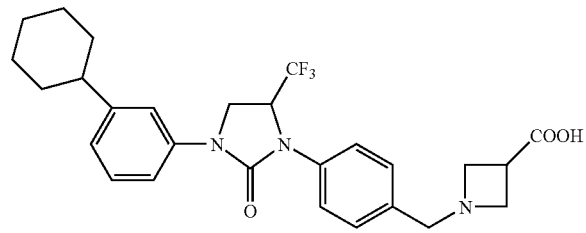

having the chemical name 1-(4-(3-(3-cyclohexylphenyl)-2-oxo-5-(trifluoromethyl)imidazolidin-1-yl)benzyl)azetidine-3-carboxylic acid,

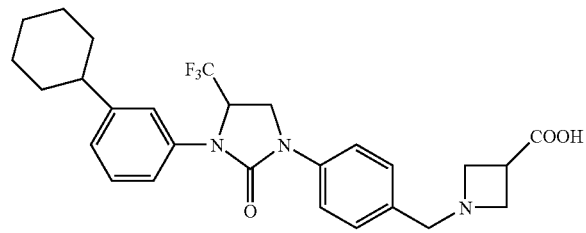

having the chemical name 1-(4-(3-(3-cyclohexylphenyl)-2-oxo-4-(trifluoromethyl)imidazolidin-1-yl)benzyl)azetidine-3-carboxylic acid, and pharmaceutically acceptable salts thereof.

In certain instances, the invention features a compound selected from the group consisting of

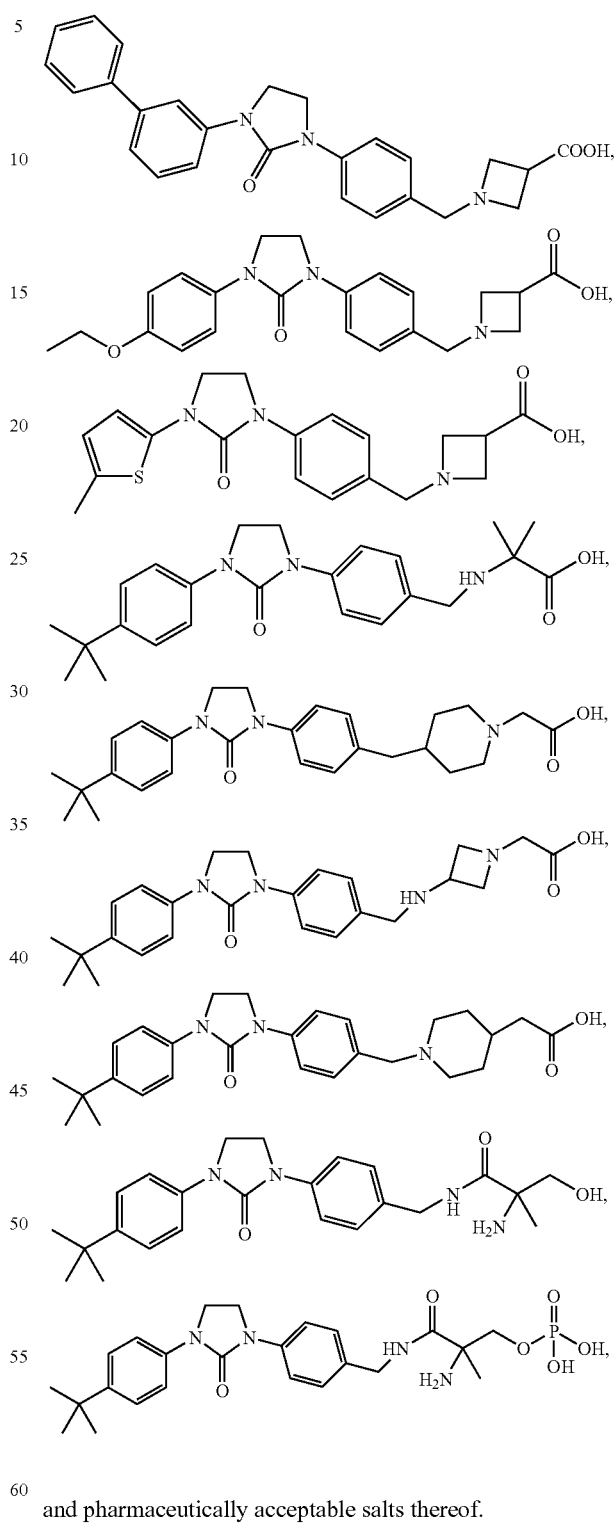

and pharmaceutically acceptable salts thereof.

The compounds of the present invention are high affinity agonists (or antagonists) at various S1P receptors. The compounds of the invention are also expected to evoke lymphopenia when introduced into rodents or humans. Thus the compounds of the invention can be used as immune modulators, and are useful in treating or preventing pathologies mediated by lymphocyte actions, including acute or chronic rejection of tissue grafts such as organ transplants, and autoimmune diseases. Autoimmune diseases that may be treated with compounds of the invention include: systemic lupus erythematosus, multiple sclerosis, Behçet's disease, glomerulonephritis, rheumatoid arthritis, inflammatory bowel diseases such as Crohn's disease and ulcerative colitis, type I diabetes, uveitis, psoriasis, myasthenia gravis, glomerulonephritis, Hashimoto's thyroiditis, autoimmune hemolytic anemia, autoimmune thrombocytopenic purpura, hepatitis and Wegner's granuloma.

The compounds of the invention are useful also in treating inflammatory disorders, including atopic asthma, inflammatory glomerular injury and ischemia-reperfusion injury.

Lysophospholipids, S1P and lysophosphatidic acid (LPA), stimulate cellular proliferation and affect numerous cellular functions by signaling through G protein-coupled endothelial differentiation gene-encoded (S1P) receptors. Accordingly, the S1P receptor modulators of the invention are anticipated to have utility in immunomodulation, e.g., in anti-angiogenesis therapy, such as in neoplastic disease treatment.

In one embodiment of the invention, a pharmaceutical composition comprising one or more of the S1P receptor agonists of the present invention is administered to a mammalian species, including humans, to enhance wound repair, improve neuronal function or enhance an immune response of that species. It has also been reported that S1P inhibits fibrosis in various organs. Accordingly, the S1P receptor agonists of the invention can be used to prevent/treat diseases associated with organ fibrosis, such as pulmonary fibrosis, interstitial pneumonia, chronic hepatitis, hepatic cirrhosis, chronic renal insufficiency or kidney glomerular sclerosis. In one embodiment, a composition comprising an S1P receptor agonist of the present invention is used to treat wounds, including burns, cuts, lacerations, surgical incisions, bed sores, and slow-healing ulcers such as those seen in diabetics.

In addition, S1P modulating compounds of the invention are believed to mobilize lymphocytes and increase their homing to secondary lymphoid tissues. Thus the present compounds can be used to direct lymphocytes away from transplanted organs, e.g., allografts, or healthy cells, e.g., pancreatic islets as in type I diabetes, myelin sheathing (multiple sclerosis), or other tissues that may be subjected to an undesirable immunoresponse, and thus decrease damage to such tissues from the immune system.

In another embodiment, the S1P receptor-modulating compounds of the invention are administered to a subject to treat or prevent a disorder of abnormal cell growth and differentiation. These disorders include Alzheimer's disease, aberrant corpus luteum formation, osteoporosis, anovulation, Parkinson's disease, and cancer. In one embodiment, an S1P antagonist is administered to a patient to treat a disease associated with abnormal growth.

In one embodiment, the compounds of the invention are used as immunomodulators to alter immune system activities and prevent damage to healthy tissue that would otherwise occur in autoimmune diseases and in organ transplantation. In particular, the compounds can be administered to patients as part of the treatment associated with organ transplantation, including pancreas, pancreatic islets, kidney, heart and lung transplantations. The S1P modulators can be administered alone or in combination with known immunosuppressants such as cyclosporine, tacrolimus, rapamycin, azathioprine, cyclophosphamide, methotrexate and corticosteroids such as cortisone, des-oxymetasone, betametasone, desametasone, flunisolide, prednisolone, prednisone, amcinomide, desonide, methylprednisolone, triamcinolone, and alclometasone.

S1P also acts as a survival factor in many cell types. In particular, compounds of the invention having S1P antagonistic activity are anticipated to be useful in protecting cells and tissues from hypoxic conditions. In accordance with one embodiment, compounds of the invention are administered to a patient judged to be or actually in need of treatment, to treat cells and tissues exposed to hypoxic conditions, including injury sustained as a result of ischemia. In accordance with one embodiment, compounds of the invention that show S1P receptor antagonist activity can be used to treat ischemia reperfusion type injury. Interference with the supply of oxygenated blood to tissues is defined as ischemia. The effects of ischemia are known to be progressive, so that over time cellular vitality continues to deteriorate and tissues become necrotic. Total persistent ischemia, with limited oxygen perfusion of tissues, results in cell death and eventually in coagulation-induced necrosis despite reperfusion with arterial blood. Evidence indicates that a significant proportion of the injury associated with ischemia is a consequence of the events associated with reperfusion of ischemic tissues, hence the term reperfusion injury.

Pharmaceutical compositions comprising the compounds of the invention may be administered to an individual in need by any number of routes, including topical, oral, intravenous, intramuscular, intra-arterial, intramedullary, intrathecal, intraventricular, transdermal, subcutaneous, intraperitoneal, intranasal, enteral, topical, sublingual, or rectal means. The oral route is typically employed for most conditions requiring the compounds of the invention. Preference is given to intravenous injection or infusion for the acute treatments. For maintenance regimens the oral or parenteral, e.g., intramuscular or subcutaneous, route is preferred. In accordance with one embodiment a composition is provided that comprises a compound of invention and albumin, e.g., a compound of the present invention, a pharmaceutically acceptable carrier and 0.1-1.0% albumin. Albumin functions as a buffer and improves the solubility of the compounds.

The invention also provides a pharmaceutical pack or kit comprising one or more containers filled with one or more of the ingredients of the pharmaceutical compositions of the invention. In accordance with one embodiment, a kit is provided for treating a patient in need of immunomodulation, including instructions for use of the kit. In this embodiment the kit comprises one or more of the S1P modulators of the invention, and may also include one or more known immunosuppressants. These pharmaceuticals can be packaged in a variety of containers, e.g., vials, tubes, microtiter well plates, bottles, and the like. Other reagents can be included in separate containers and provided with the kit; e.g., positive control samples, negative control samples, buffers, cell culture media, etc. Preferably, the kits will also include instructions for use.

The activity of compounds of the invention may be determined by using an assay for detecting S1P receptor activity (such as the [γ-35 S]GTP binding assay) and assaying for activity in the presence of S1P and the test compound. More particularly, in the method described by Traynor et al., 1995, *Mol. Pharmacol.* 47: 848-854, incorporated herein by reference, G-protein coupling to membranes can be evaluated by measuring the binding of labeled GTP.

For example, samples comprising membranes isolated from cells expressing an S1P polypeptide can be incubated in a buffer promoting binding of the polypeptide to ligand (i.e. S1P), in the presence of radiolabeled GTP and unlabeled GDP (e.g., in 20 mM HEPES, pH 7.4, 100 mM NaCl, and 10 mM $MgCl_2$, 80 pM $^{35}$S-GTP$_\gamma$S and 3 μM GDP), with and without a candidate modulator. The assay mixture is incubated for a suitable period of time to permit binding to and activation of the receptor (e.g., 60 minutes at 30° C.), after which time unbound labeled GTP is removed (e.g., by filtration onto GF/B filters). Bound, labeled GTP can be measured by liquid scintillation counting. A decrease of 10% or more in labeled GTP binding as measured by scintillation counting in a sample containing a candidate modulator, relative to a sample without the modulator, indicates that the candidate modulator is an inhibitor of S1P receptor activity.

A similar GTP-binding assay can be performed without the presence of the ligand (S1P) to identify agents that act as agonists. In this case, ligand-stimulated GTP binding is used as a standard. An agent is considered an agonist if it induces at least 50% of the level of GTP binding induced by S1P when the agent is present at 10 μm or less, and preferably will induce a level which is the same as or higher than that induced by the ligand.

GTPase activity can be measured by incubating cell membrane extracts containing an S1P receptor with $\gamma^{32}$P-GTP. Active GTPase will release the label as inorganic phosphate, which can be detected by separation of free inorganic phosphate in a 5% suspension of activated charcoal in 20 mM $H_3PO_4$, followed by scintillation counting. Controls would include assays using membrane extracts isolated from cells not expressing an S1P receptor (e.g., mock-transfected cells), in order to exclude possible non-specific effects of the candidate modulator. In order to assay for the effect of a candidate modulator on S1P-regulated GTPase activity, cell membrane samples can be incubated with the ligand (S1P), with and without the modulator, and a GTPase assay can be performed as described above. A change (increase or decrease) of 10% or more in the level of GTP binding or GTPase activity relative to samples without modulator is indicative of S1P modulation by a candidate modulator.

Identified S1P receptor agonists and antagonists can be used to treat a variety of human diseases and disorders, including, but not limited to the treatment of infections such as bacterial, fungal, protozoan and viral infections, particularly infections caused by HIV-1 or HIV-2; pain; cancers; diabetes, obesity; anorexia; bulimia; asthma; Parkinson's disease; acute heart failure; hypotension; hypertension; urinary retention; osteoporosis; angina pectoris; myocardial infarction; stroke; ulcers; asthma; allergy; benign prostatic hypertrophy; migraine; vomiting; psychotic and neurological disorders, including anxiety, schizophrenia, manic depression, depression, delirium, dementia, and severe mental retardation.

Pain is a complex subjective sensation reflecting real or potential tissue damage and the affective response to it. Acute pain is a physiological signal indicating a potential or actual injury. Chronic pain can either be somatogenetic (organic) or psychogenic. Chronic pain is frequently accompanied or followed by vegetative signs, which often result in depression.

Somatogenetic pain may be of nociceptive origin, inflammatory or neuropathic. Nociceptive pain is judged to be commensurate with ongoing activation of somatic or visceral pain-sensitive nerve fibers. Neuropathic pain results from dysfunction in the nervous system; it is believed to be sustained by aberrant somatosensory processes in the peripheral nervous system, the CNS, or both. Chronic pain results in individual suffering and social economic costs of tremendous extent. Existing pharmacological pain therapies are widely unsatisfying both in terms of efficacy and of safety.

In one embodiment, S1P modulators of the present invention are used as immunomodulators to suppress the immune system and prevent damage to healthy tissue that would otherwise occur in autoimmune diseases and in organ transplantation. The compounds can be administered to patients as part of the treatment associated with organ transplantation, including pancreas, pancreatic islets, kidney, heart and lung transplantations. The S1P modulators can be administered alone or in combination with known immunosuppressants such as cyclosporine, tacrolimus, azatioprine, desoxymetasone, cyclophosphamide, cortisone, betametasone, FK 506 (a fungal macrolide immunosuppressant), desametasone, flunisolide, prednisolone, prednisone, amcinomide desonide, methylprednisolone, triamcinolone, alclometasone and methotrexate.

The dosage to be used is, of course, dependent on the specific disorder to be treated, as well as additional factors including the age, weight, general state of health, severity of the symptoms, frequency of the treatment and whether additional pharmaceuticals accompany the treatment. The dosages are in general administered several times per day and preferably one to three times per day. The amounts of the individual active compounds are easily determined by routine procedures known to those of ordinary skill in the art S1P also acts as a survival factor in many cell types. S1P receptor modulators are anticipated to have activity in protecting cells and tissues from hypoxic conditions. In accordance with one embodiment compounds of the invention are administered to treat cells and tissues exposed to hypoxic conditions, including injury sustained as a result of ischemia. In accordance with one embodiment, the S1P modulators having antagonistic activity can be used to treat ischemia reperfusion type injury. Interference with the supply of oxygenated blood to tissues is defined as ischemia. The effects of ischemia are known to be progressive, such that over time cellular vitality continues to deteriorate and tissues become necrotic. Total persistent ischemia, with limited oxygen perfusion of tissues, results in cell death and eventually in coagulation-induced necrosis despite reperfusion with arterial blood.

The compounds of the invention and the other pharmacologically active agent may be administered to a patient simultaneously, sequentially or in combination. It will be appreciated that when using a combination of the invention, the compound of the invention and the other pharmacologically active agent may be in the same pharmaceutically acceptable carrier and therefore administered simultaneously. They may be in separate pharmaceutical carriers such as conventional oral dosage forms which are taken simultaneously. The term "combination" further refers to the case where the compounds are provided in separate dosage forms and are administered sequentially.

The compounds of the invention may be administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician.

An appropriate dosage level will generally be about 0.001 to 50 mg per kg patient body weight per day, which may be administered in single or multiple doses. Preferably, the dosage level will be about 0.01 to about 25 mg/kg per day; more preferably about 0.05 to about 10 mg/kg per day. For example, in the treatment or prevention of a disorder of the central nervous system, a suitable dosage level is about 0.001 to 10 mg/kg per day, preferably about 0.005 to 5 mg/kg per day, and especially about 0.01 to 1 mg/kg per day. The compounds may be administered on a regimen of 1 to 4 times per day, preferably once or twice per day.

It will be appreciated that the amount of the compound of the invention required for use in any treatment will vary not only with the particular compounds or composition selected but also with the route of administration, the nature of the condition being treated, and the age and condition of the patient, and will ultimately be at the discretion of the attendant physician.

The compositions and combination therapies of the invention may be administered in combination with a variety of pharmaceutical excipients, including stabilizing agents, carriers and/or encapsulation formulations as described herein.

Aqueous compositions of the present invention comprise an effective amount of the compounds of the invention, dissolved or dispersed in a pharmaceutically acceptable carrier or aqueous medium.

"Pharmaceutically or pharmacologically acceptable" include molecular entities and compositions that do not produce an adverse, allergic or other untoward reaction when administered to an animal, or a human, as appropriate. "Pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For human administration, preparations should meet sterility, pyrogenicity, general safety and purity standards as required by FDA Office of Biologics standards.

The compositions and combination therapies of the invention will then generally be formulated for parenteral administration, e.g., formulated for injection via the intravenous, intramuscular, subcutaneous, intralesional, or even intraperitoneal routes. The preparation of an aqueous composition that contains a composition of the invention or an active component or ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Solutions of active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

Therapeutic or pharmacological compositions of the present invention will generally comprise an effective amount of the component(s) of the combination therapy, dissolved or dispersed in a pharmaceutically acceptable medium. Pharmaceutically acceptable media or carriers include any and all solvents, dispersion media, coatings, antibacterial and antifungal agents, isotonic and absorption delaying agents and the like. The use of such media and agents for pharmaceutical active substances is well known in the art. Supplementary active ingredients can also be incorporated into the therapeutic compositions of the present invention.

The preparation of pharmaceutical or pharmacological compositions will be known to those of skill in the art in light of the present disclosure. Typically, such compositions may be prepared as injectables, either as liquid solutions or suspensions; solid forms suitable for solution in, or suspension in, liquid prior to injection; as tablets or other solids for oral administration; as time release capsules; or in any other form currently used, including cremes, lotions, mouthwashes, inhalants and the like.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly, concentrated solutions for intramuscular injection is also contemplated. In this regard, the use of DMSO as solvent is preferred as this will result in extremely rapid penetration, delivering high concentrations of the active compound(s) or agent(s) to a small area.

The use of sterile formulations, such as saline-based washes, by surgeons, physicians or health care workers to cleanse a particular area in the operating field may also be particularly useful. Therapeutic formulations in accordance with the present invention may also be reconstituted in the form of mouthwashes, or in conjunction with antifungal reagents. Inhalant forms are also envisioned. The therapeutic formulations of the invention may also be prepared in forms suitable for topical administration, such as in cremes and lotions.

Suitable preservatives for use in such a solution include benzalkonium chloride, benzethonium chloride, chlorobutanol, thimerosal and the like. Suitable buffers include boric acid, sodium and potassium bicarbonate, sodium and potassium borates, sodium and potassium carbonate, sodium acetate, sodium biphosphate and the like, in amounts sufficient to maintain the pH at between about pH 6 and pH 8, and preferably, between about pH 7 and pH 7.5. Suitable tonicity agents are dextran 40, dextran 70, dextrose, glycerin, potassium chloride, propylene glycol, sodium chloride, and the like, such that the sodium chloride equivalent of the ophthalmic solution is in the range 0.9 plus or minus 0.2%. Suitable antioxidants and stabilizers include sodium bisulfite, sodium metabisulfite, sodium thiosulfite, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose and the like.

Upon formulation, therapeutics will be administered in a manner compatible with the dosage formulation, and in such amount as is pharmacologically effective. The formulations are easily administered in a variety of dosage forms, such as the type of injectable solutions described above, but drug release capsules and the like can also be employed.

In this context, the quantity of active ingredient and volume of composition to be administered depends on the host animal to be treated. Precise amounts of active compound required for administration depend on the judgment of the practitioner and are peculiar to each individual.

A minimal volume of a composition required to disperse the active compounds is typically utilized. Suitable regimes for administration are also variable, but would be typified by initially administering the compound and monitoring the results and then giving further controlled doses at further intervals. For example, for parenteral administration, a suitably buffered, and if necessary, isotonic aqueous solution would be prepared and used for intravenous, intramuscular, subcutaneous or even intraperitoneal administration. One dosage could be dissolved in 1 ml of isotonic NaCl solution and either added to 1000 ml of hypodermolysis fluid or injected at the proposed site of infusion, (see for example, *Remington's Pharmaceutical Sciences* 15th Edition, pages 1035-1038 and 1570-1580).

In certain embodiments, active compounds may be administered orally. This is contemplated for agents which are generally resistant, or have been rendered resistant, to proteolysis by digestive enzymes. Such compounds are contemplated to include chemically designed or modified agents; dextrorotatory peptides; and peptide and liposomal formulations in time release capsules to avoid peptidase and lipase degradation.

Pharmaceutically acceptable salts include acid addition salts and which are formed with inorganic acids such as, for example, hydrochloric, hydrobromic, boric, phosphoric, sulfuric acids or phosphoric acids, or such organic acids as acetic, oxalic, tartaric, maleic, fumaric, citric, succinic, mesylic, mandelic, succinic, benzoic, ascorbic, methanesulphonic, a-keto glutaric, a-glycerophosphoric, glucose-1-phosphoric acids and the like. Salts formed with the free carboxyl groups can also be derived from inorganic bases such as, for example, sodium, potassium, ammonium, calcium, magnesium, or ferric hydroxides, and such organic bases as isopropylamine, trimethylamine, histidine, procaine and the like. Other examples of pharmaceutically acceptable salts include quaternary derivatives, and internal salts such as N-oxides.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze drying techniques which yield a powder of the active ingredient plus any additional desired ingredient from a previously sterile-filtered solution thereof.

The preparation of more, or highly, concentrated solutions for direct injection is also contemplated, where the use of DMSO as solvent is envisioned to result in extremely rapid penetration, delivering high concentrations of the active agents to a small area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure.

In addition to the compounds formulated for parenteral administration, such as intravenous or intramuscular injection, other pharmaceutically acceptable forms include, e.g., tablets or other solids for oral administration; liposomal formulations; time-release capsules; and any other form currently used, including cremes.

Additional formulations suitable for other modes of administration include suppositories. For suppositories, traditional binders and carriers may include, for example, polyalkylene glycols or triglycerides; such suppositories may be formed from mixtures containing the active ingredient in the range of 0.5% to 10%, preferably 1%-2%.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders.

In certain defined embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor.

The pharmaceutical compositions of this invention may be used in the form of a pharmaceutical preparation, for example, in solid, semisolid or liquid form, which contains one or more of the compound of the invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active object compound is included in the pharmaceutical composition in an amount sufficient to produce the desired effect upon the process or condition of the disease.

For preparing solid compositions such as tablets, the principal active ingredient is mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compositions of the invention may be incorporated for administration orally or by injection include aqueous solution, suitably flavored syrups, aqueous or oil suspensions, and emulsions with acceptable oils such as cottonseed oil, sesame oil, coconut oil or peanut oil, or with a solubilizing or emulsifying agent suitable for intravenous use, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulized by use of inert gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

For treating clinical conditions and diseases noted above, the compound of this invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

The following examples are given for the purpose of illustrating the invention, but not for limiting the scope or spirit of the invention.

Compounds of the invention, including those specifically disclosed hereinabove and hereinbelow, may be prepared as described in the following schemes. For example, the compounds of formula I may be prepared as described in Schemes 1, 2, and 3 below, which are known to those of skill in the art for making fragments and combinations thereof.

Scheme 1

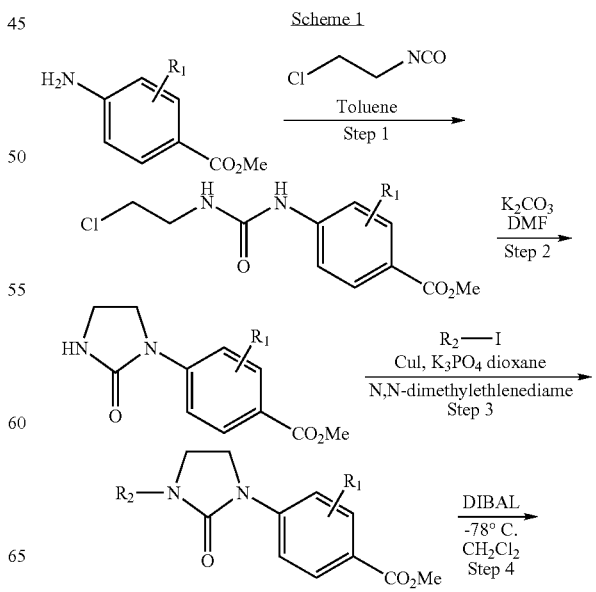

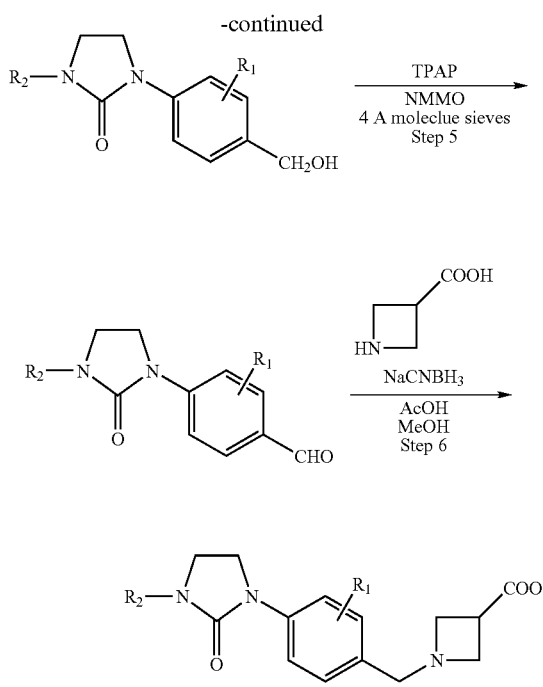
wherein, the definition of $R^1$ is as defined in the Summary of the Invention, and $R^2$ is substituted aryl or substituted heteroaryl.
Scheme 2
wherein, the definition of $R^1$ and p are as defined in the Summary of the Invention, and $R^2$ is substituted aryl or substituted heteroaryl.
Scheme 3
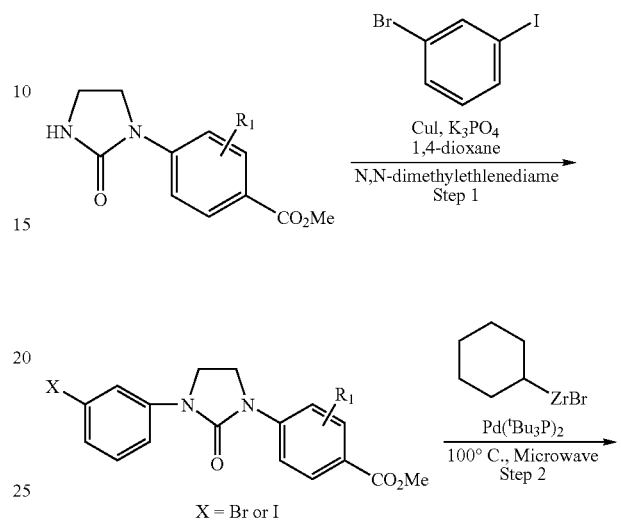
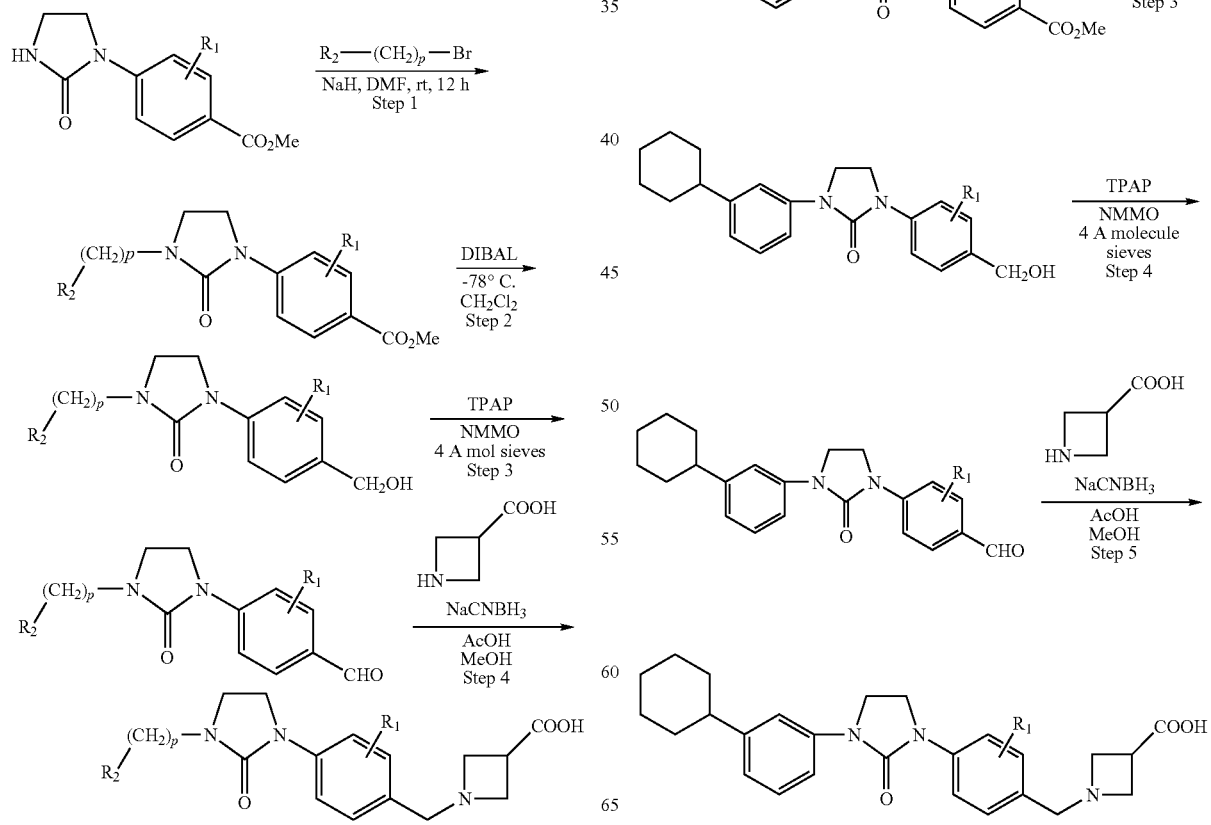

wherein, the definition of $R^1$ and p are as defined in the Summary of the Invention, and $R^2$ is substituted aryl or substituted heteroaryl.

EXAMPLES

Compound 1

1-(4-(3-(4-tert-Butylphenyl)-2-oxoimidazolidin-1-yl)benzyl)azetidine-3-carboxylic acid Methyl 4-(3-(2-chloroethyl)ureido)benzoate (Step 1 in Scheme 1)

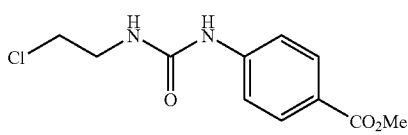

To a solution of methyl 4-aminobenzoate (6.05 g, 40 mmole) in dry toluene (100 ml) was added 2-chloroethylisocyante (4.65 g, 44 mmole). The mixture was stirred at 40° C. for 12 hours. After cooling to room temperature, the solid was collected by filtration and washed with toluene, water and dried in air to provide methyl 4-(3-(2-chloroethyl)ureido)benzoate (8.72 g, 85%) as a white solid without further purification for the next step.

Methyl 4-(2-oxoimidazolidin-1-yl)benzoate (Step 2 in Scheme 1)

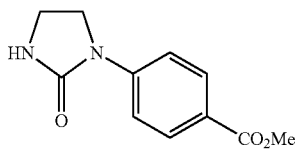

Methyl 4-(3-(2-chloroethyl)ureido)benzoate (8.5 g, 33.1 mmol) was then stirred in N,N-dimethylformamide (80 ml) with $K_2CO_3$ (2.3 g, 16.7 mmol) at room temperature for 12 hours. The solid was filtered off and the solvent was removed in vacuum. The crude product was dissolved in dichloromethane and purified on ISCO system (30% EtOAc in dichloromethane) to give a pure product as a white crystalline (5.48 g, 75%): $^1$H NMR (400 MHz, CDCl$_3$) δ 8.00 (d, 2H), 7.62 (d, 2H), 4.90 (br s, 1H), 3.97 (dd, 2H), 3.90 (s, 3H), 3.60 (dd, 2H). MS (ESI) m/z: Calculated: 220.08; Observed: 221.10 (M$^+$+1).

Methyl 4-(3-(4-tert-butylphenyl)-2-oxoimidazolidin-1-yl)benzoate (Step 3 in Scheme 1)

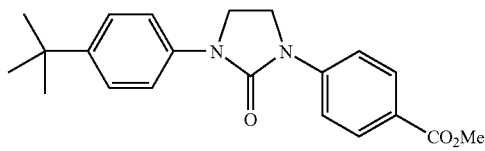

Methyl 4-(2-oxoimidazolidin-1-yl)benzoate (220 mg, 1.0 mmole) was mixed with iodo-1-tert-butyl-4-iodobenzene (260 mg, 1.0 mmol), CuI (38 mg, 0.2 mmol), $K_3PO_4$ (426 mg, 2 mmol), N,N'-dimethyl ethylenediamine (17 mg, 0.2 mmol) and 1,4-dioxane (5 ml). The mixture was heated at 110° C. with stirring for 12 hours, and the solvent was removed in vacuum. The residue was suspended in dichloromethane and purified on ISCO system (5% methanol in dichloromethane) to give a pure product as a white crystalline (275 mg, 78%): $^1$H NMR (400 MHz, CDCl$_3$) δ 8.05 (dd, 2H), 7.70 (dd, 2H), 7.36 (dd, 2H), 7.20 (dd, 2H), 4.02 (s, 4H), 3.90 (s, 3H), 1.30 (s, 9H). MS (ESI) m/z: Calculated: 352.18; Observed: 353.10 (M$^+$+1).

1-(4-tert-Butylphenyl)-3-(4-(hydroxymethyl)phenyl)imidazolidin-2-one (Step 4 in Scheme 1)

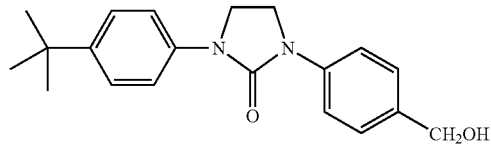

A solution of methyl 4-(3-(4-tert-butylphenyl)-2-oxoimidazolidin-1-yl)benzoate (270 mg, 0.77 mmol) in dichloromethane (50 ml) at −78° C. was treated with ml of 1.0 M DIBAL solution in dichloromethane. The resulting solution was stirred cold for 2 hour, then quenched with ml of sat's Rochelle salt solution. The mixture was partitioned between 100 ml dichloromethane and 50 ml of 1 N NaOH. The organic layer was separated, dried and concentrated. The residue was purified on ISCO system (5% methanol in dichloromethane) to give a pure product as a white crystalline (113 mg, 35%): $^1$H NMR (400 MHz, CDCl$_3$) δ 7.60 (d, 2H), 7.50 (d, 2H), 7.10 (m, 4H), 4.64 (s, 2H), 4.00 (s, 4H), 1.58 (s, 9H).

4-(3-(4-tert-Butylphenyl)-2-oxoimidazolidin-1-yl)benzaldehyde (Step 5 in Scheme 1)

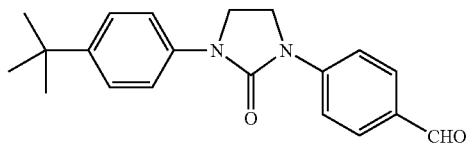

A mixture of 1-(4-tert-butylphenyl)-3-(4-(hydroxymethyl)phenyl)imidazolidin-2-one (100 mg, 0.31 mmol), 4-methylmorpholine N-oxide (72 mg, 0.62 mmol), and 4 A molecular sieves (100 mg) in 10 ml of acetonitrile was treated with tetrapropylammonium perruthnate and the resulting mixture was stirred at room temperature for 3 hours. The solids were filtered and the filtrated was concentrated. The residue was purified on ISCO system (2% methanol in dichloromethane) to give a pure product as a white crystalline (72 mg, 73%): $^1$H NMR (400 MHz, CDCl$_3$) δ 9.93 (s, 1H), 7.81 (d, 2H), 7.79 (d, 2H), 7.50 (d, 2H), 7.40 (d, 2H), 4.03 (s, 4H), 1.33 (s, 9H). MS (ESI) m/z: Calculated: 322.17; Observed: 323.1 (M$^+$+1).

1-(4-(3-(4-tert-Butylphenyl)-2-oxoimidazolidin-1-yl)benzyl)azetidine-3-carboxylic acid (Step 6 in Scheme 1)

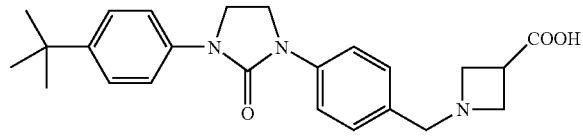

A mixture of 4-(3-(4-tert-butylphenyl)-2-oxoimidazolidin-1-yl)benzaldehyde (32 mg, 0.1 mmol), acetic acid (50 μl) and azetidine-3-carboxylic acid (13 mg, 0.13 mmol) in dichloromethane/MeOH (1:1, 5 mL) was stirred at room temperature for 1 hour. Sodium cyanoborohydride (3.5 mg, 0.05 mmol) was added and the reaction mixture was stirred for 6 hour at room temperature. After concentration of solvent under reduced pressure, the resulting residue was dissolved in dimethylsulfoxide, filtered and purified by reverse phase preparative HPLC (Phenomenex reverse phase Luna 5u C18(2) column, 60×21.2 mm ID, mobile phase: A=0.05% TFA in water; B=0.05% TFA in acetonitrile. The flow rate was 10-12 mL/min) to yield the title product 4 mg (10%): $^1$H NMR (400 MHz, CDOD$_3$) δ 7.72 (d, 2H), 7.51-7.40 (m, 6H), 4.33 (s, 2H), 4.28 (m, 4H), 4.02 (s, 4H), 3.64 (m, 1H), 1.32 (s, 9H). MS (ESI) m/z: Calculated: 407.22; Observed: 408.00 (M$^+$+1).

Compound 2

1-(4-(3-(4-tert-butylbenzyl)-2-oxoimidazolidin-1-yl)benzyl)azetidine-3-carboxylic acid (Scheme 2)

Methyl 4-(3-(4-tert-butylbenzyl)-2-oxoimidazolidin-1-yl)benzoate

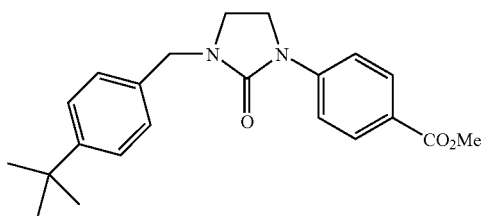

To a solution of methyl 4-(2-oxoimidazolidin-1-yl)benzoate (440 mg, 2.0 mmol) in N,N-dimethylformamide (10 ml) at 0° C. was added sodium hydride (96 mg-60% in oil, 2.4 mmole). The resulting mixture was stirred for 1 hour followed by addition of 1-(bromomethyl)-4-tert-butylbenzene (545 mg, 2.4 mmol). After stirring 24 hours at room temperature, the mixture was quenched with 1 ml water and the solvents were removed under reduced pressure. The residue was diluted with ethyl acetate (50 ml) and washed with water (50 ml) and brine (50 ml). Removal of the solvent gave the residue which was purified on ISCO system (1% methanol in dichloromethane) to give a pure product as a white solid (593 mg, 81%): $^1$H NMR (400 MHz, CDCl$_3$) δ 8.25 (d, 2H), 7.68 (d, 2H), 7.36 (d, 2H), 7.23 (d, 2H), 4.46 (s, 2H), 3.90 (s, 3H), 3.83 (dd, 2H), 3.43 (dd, 2H), 1.31 (s, 9H). MS (ESI) m/z: Calculated: 366.19; Observed: 367.1 (M$^+$+1).

1-(4-tert-Butylbenzyl)-3-(4-(hydroxymethyl)phenyl)imidazolidin-2-one

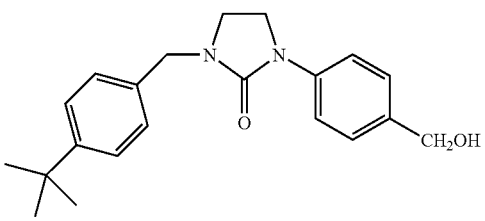

The title compound was prepared as Example Compound 1 (step 4) described above (62% yield): $^1$H NMR (400 MHz, CDCl$_3$) δ 7.59 (d, 2H), 7.38 (m, 4H), 7.24 (d, 2H), 4.65 (s, 2H), 4.44 (s, 2H), 3.81 (dd, 2H), 3.39 (dd, 2H), 1.32 (s, 9H).

4-(3-(4-tert-Butylbenzyl)-2-oxoimidazolidin-1-yl)benzaldehyde

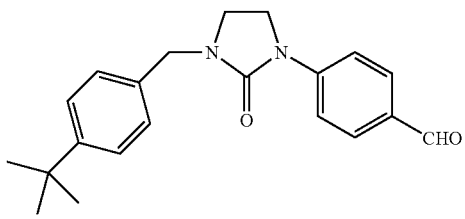

The title compound was prepared as Example Compound 1 (step 5) described above (65% yield): $^1$H NMR (400 MHz, CDCl$_3$) δ 9.90 (s, 1H), 7.88 (d, 2H), 7.78 (d, 2H), 7.39 (d, 2H), 7.24 (d, 2H), 4.47 (s, 2H), 3.88 (dd, 2H), 3.45 (dd, 2H), 1.32 (s, 9H). MS (ESI) m/z: Calculated: 336.18; Observed: 337.1 (M$^+$+1).

1-(4-(3-(4-tert-butylbenzyl)-2-oxoimidazolidin-1-yl)benzyl)azetidine-3-carboxylic acid

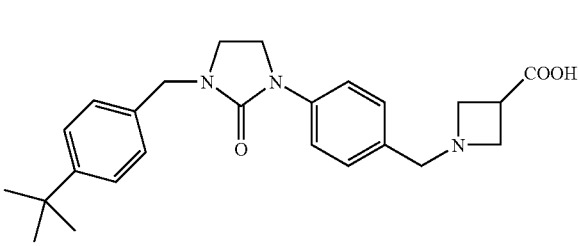

The title compound was prepared using a procedure analogous to Compound 1 (step 6) described above (28% yield): $^1$H NMR (400 MHz, CDOD$_3$) δ 7.68 (d, 2H), 7.40 (m, 4H), 7.22 (d, 2H), 4.42 (s, 2H), 4.38 (s, 2H), 4.30 (m, 4H), 3.82 (dd, 2H), 3.60 (m, 1H), 3.42 (dd, 2H), 1.31 (s, 9H). MS (ESI) m/z: Calculated: 421.24; Observed: 421.90 (M$^+$+1).

Compound 3

1-(4-(3-(4-Butylphenyl)-2-oxoimidazolidin-1-yl)benzyl)azetidine-3-carboxylic acid (Scheme 1)

Methyl 4-(3-(4-butylphenyl)-2-oxoimidazolidin-1-yl)benzoate

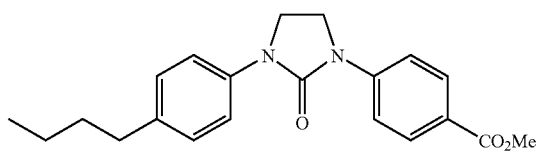

The title compound was prepared as Example Compound 1 (step 3) described above (64% yield): $^1$H NMR (400 MHz, CDCl$_3$): δ 8.06 (d, 2H), 7.70 (d, 2H), 7.50 (d, 2H), 7.21 (d, 2H), 4.00 (s, 4H), 3.91 (s, 3H), 2.62 (t, 2H), 1.56 (m, 2H), 1.34 (m, 2H), 0.94 (t, 3H). MS (ESI) m/z: Calculated: 352.18; Observed: 353.20 (M$^+$+1).

1-(4-Butylphenyl)-3-(4-(hydroxymethyl)phenyl)imidazolidin-2-one

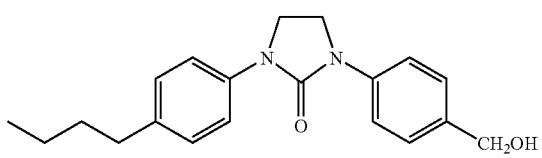

The title compound was prepared as Example Compound 1 (step 4) described above (72% yield): $^1$H NMR (400 MHz, CDCl$_3$) δ 7.60 (d, 2H), 7.50 (d, 2H), 7.38 (d, 2H), 7.20 (d, 2H), 4.62 (s, 2H), 4.00 (s, 4H), 2.60 (t, 2H), 1.60 (m, 2H), 1.38 (m, 2H), 0.90 (t, 3H). MS (ESI) m/z: Calculated: 324.18; Observed: 325.2 (M$^+$+1).

4-(3-(4-Butylphenyl)-2-oxoimidazolidin-1-yl)benzaldehyde

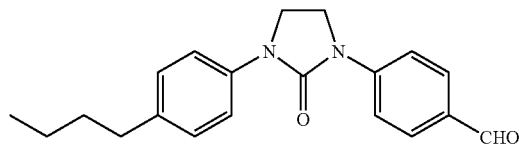

The title compound was prepared as Example Compound 1 (step 5) described above (70% yield): $^1$H NMR (400 MHz, CDCl$_3$) δ 9.65 (s, 1H), 7.90 (d, 2H), 7.87 (d, 2H), 7.49 (d, 2H), 7.21 (d, 2H), 4.01 (s, 4H), 2.61 (t, 2H), 1.59 (m, 2H), 1.38 (m, 2H), 0.92 (t, 3H). MS (ESI) m/z: Calculated: 322.17; Observed: 323.2 (M$^+$+1).

1-(4-(3-(4-Butylphenyl)-2-oxoimidazolidin-1-yl)benzyl)azetidine-3-carboxylic acid

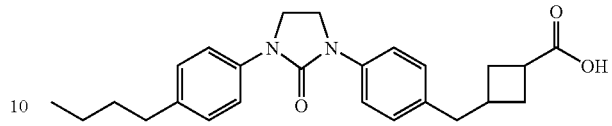

The title compound was prepared as Example Compound 1 (step 6) described above (23% yield): $^1$H NMR (400 MHz, CD$_3$OD) δ 7.72 (d, 2H), 7.47 (m, 4H), 7.18 (d, 2H), 4.36 (s, 2H), 4.27 (m, 4H), 4.02 (s, 4H), 3.63 (m, 1H), 2.60 (dd, 2H), 1.59 (m, 2H), 1.34 (m, 2H), 0.94 (t, 3H). MS (ESI) m/z: Calculated: 407.22; Observed: 408.10 (M$^+$+1).

Compound 4

1-(4-(3-(3-tert-Butylphenyl)-2-oxoimidazolidin-1-yl)benzyl)azetidine-3-carboxylic acid (Scheme 1)

Methyl 4-(3-(3-tert-butylphenyl)-2-oxoimidazolidin-1-yl)benzoate

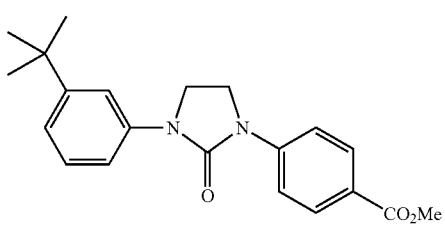

The title compound was prepared as Example Compound 1 (step 3) described above (57% yield): $^1$H NMR (400 MHz, CDCl$_3$) δ 8.06 (d, 2H), 7.74 (m, 3H), 7.31 (m, 2H), 7.18 (d, 2H), 4.02 (s, 4H), 3.91 (s, 3H), 1.34 (s, 9H). MS (ESI) m/z: Calculated: 352.18; Observed: 353.10 (M$^+$+1).

1-(3-tert-Butylphenyl)-3-(4-(hydroxymethyl)phenyl)imidazolidin-2-one

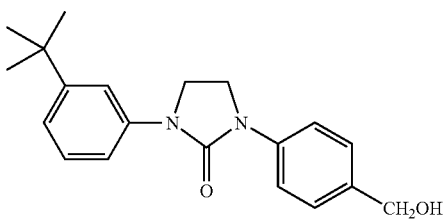

The title compound was prepared as Example Compound 1 (step 4) described above (76% yield): $^1$H NMR (400 MHz, CDCl$_3$) δ 7.76 (s, 1H), 7.60 (d, 2H), 7.38 (d, 2H), 7.31 (m, 2H), 7.15 (d, 1H), 4.68 (s, 2H), 4.00 (s, 4H), 1.34 (s, 9H).

4-(3-(3-tert-Butylphenyl)-2-oxoimidazolidin-1-yl)benzaldehyde

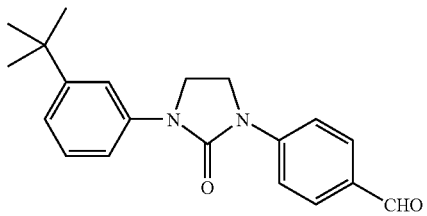

The title compound was prepared as Example Compound 1 (step 5) described above (78% yield): $^1$H NMR (400 MHz, CDCl$_3$) δ 9.95 (s, 1H), 7.90 (d, 2H), 7.80 (d, 2H), 7.75 (s, 1H), 7.35 (m, 2H), 7.19 (dd, 1H), 4.04 (s, 4H), 1.34 (s, 9H). MS (ESI) m/z: Calculated: 322.17; Observed: 323.1 (M$^+$+1).

1-(4-(3-(3-tert-Butylphenyl)-2-oxoimidazolidin-1-yl)benzyl)azetidine-3-carboxylic acid

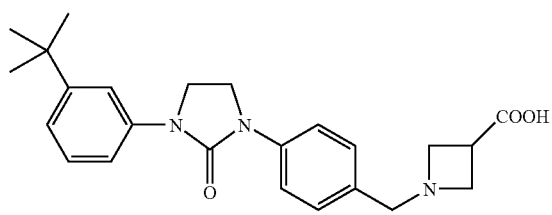

The title compound was prepared using a procedure analogous to Compound 1 (step 6) described above (6% yield): $^1$H NMR (400 MHz, CDOD$_3$) δ 7.73 (m, 3H), 7.46 (d, 2H), 7.30 (m, 2H), 7.18 (m, 1H), 4.37 (s, 2H), 4.29 (m, 4H), 4.04 (s, 4H), 3.60 (m, 1H), 1.37 (s, 9H). MS (ESI) m/z: Calculated: 407.22; Observed: 407.90 (M$^+$+1).

Compound 5

1-(4-(2-oxo-3-(3-(Trifluoromethyl)phenyl)imidazolidin-1-yl)benzyl)azetidine-3-carboxylic acid (Scheme 1)

Methyl 4-(2-oxo-3-(3-(trifluoromethyl)phenyl)imidazolidin-1-yl)benzoate

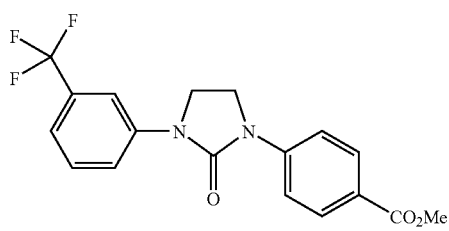

The title compound was prepared using a procedure analogous to Compound 1 (step 3) described above (58% yield): $^1$H NMR (400 MHz, CDCl$_3$) δ 8.08 (d, 2H), 8.05 (d, 2H), 7.71 (d, 2H), 7.52 (dd, 1H), 7.38 (d, 1H), 4.06 (s, 4H), 3.92 (s, 3H). MS (ESI) m/z: Calculated: 364.10; Observed: 365.1 (M$^+$+1).

1-(4-(Hydroxymethyl)phenyl)-3-(3-(trifluoromethyl)phenyl)imidazolidin-2-one

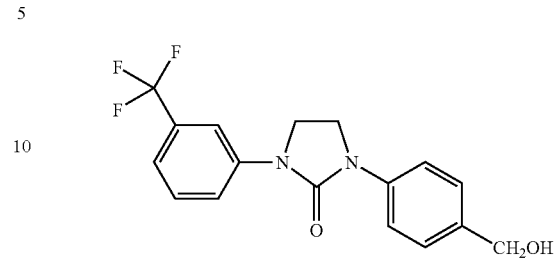

The title compound was prepared using a procedure analogous to Compound 1 (step 4) described above (67% yield): $^1$H NMR (400 MHz, CDCl$_3$) δ 7.87 (m, 2H), 7.61 (d, 2H), 7.51 (dd, 1H), 7.41 (m, 3H), 4.70 (d, 2H), 4.03 (s, 4H).

4-(2-Oxo-3-(3-(trifluoromethyl)phenyl)imidazolidin-1-yl)benzaldehyde

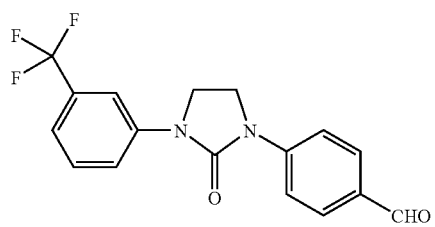

The title compound was prepared using a procedure analogous to Compound 1 (step 5) described above (76% yield): $^1$H NMR (400 MHz, CDCl$_3$) δ 9.91 (s, 1H), 7.79-7.93 (m, 6H), 754 (dd, 1H), 7.40 (d, 1H), 4.09 (s, 4H). MS (ESI) m/z: Calculated: 334.09; Observed: 335.1 (M$^+$+1).

1-(4-(2-Oxo-3-(3-(trifluoromethyl)phenyl)imidazolidin-1-yl)benzyl)azetidine-3-carboxylic acid

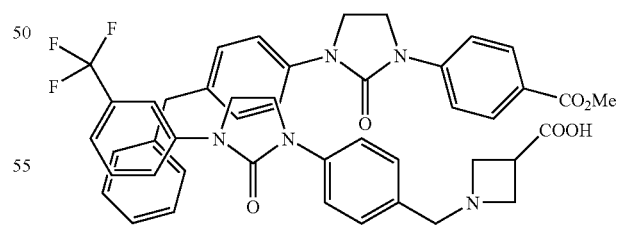

The title compound was prepared using a procedure analogous to Compound 1 (step 6) described above: $^1$H NMR (400 MHz, CDOD$_3$) δ 8.13 (S, 1H), 7.66 (m, 3H), 7.57 (dd, 1H), 7.48 (dd, 2H), 7.39 (d, 1H), 4.38 (s, 2H), 4.29 (m, 4H), 3.90 (s, 4H), 3.65 (m, 1H). MS (ESI) m/z: Calculated: 419.15; Observed: 419.90 (M$^+$+1).

Compound 6

1-(4-(3-(4-Benzylphenyl)-2-oxoimidazolidin-1-yl)benzyl)azetidine-3-carboxylic acid (Scheme 1)

Methyl 4-(3-(4-benzylphenyl)-2-oxoimidazolidin-1-yl)benzoate

Methyl 4-(2-oxoimidazolidin-1-yl)benzoate (389 mg, 1.76 mmol) was mixed with 1-benzyl-4-iodobenzene (473 mg, 1.60 mmol), CuI (77 mg, 0.40 mmol), $K_3PO_4$ (685 mg, 3.21 mmol), N,N'-dimethylethylenediamine (42 mL, 0.40 mmol), NMP (12 mL) and DMF (3 mL) in a microwave reaction tube. The mixture was heated at 100° C. for 60 min under microwave irradiation (Personal Chemistry Emrys™ Optimizer microwave reactor). Upon completion of the reaction, the solids were filtered out. The clear filtrate was then treated with MeOH causing the precipitation of methyl 4-(3-(4-benzylphenyl)-2-oxoimidazolidin-1-yl)benzoate as a pure product (44% yield): $^1$H NMR (400 MHz, $CDCl_3$) δ 8.04 (d, J=9.2, 2H), 7.68 (d, J=8.8, 2H), 7.50 (d, J=8.4, 2H), 7.31-7.18 (m, 7H), 4.00-3.97 (m, 6H), 3.90 (s, 3H). MS (ESI) m/z: Calculated: 386.44; Observed: 387.3 ($M^+$+1).

1-(4-Benzylphenyl)-3-(4-(hydroxymethyl)phenyl)imidazolidin-2-one

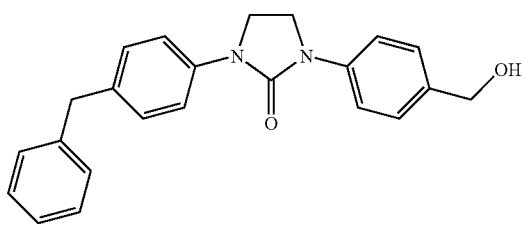

The title compound was prepared as Compound 1 (step 4 in scheme 1) in the general method described above (56% yield): $^1$H NMR (400 MHz, $CDCl_3$) δ 7.60 (d, J=9.0, 2H), 7.52 (d, J=9.0, 2H), 7.38 (d, J=8.6, 2H), 7.31-7.18 (m, 7H), 4.68 (d, J=5.9, 2H), 3.98 (br s, 6H). MS (ESI) m/z: Calculated: 358.43; Observed: 359.2 ($M^+$+1).

4-(3-(4-Benzylphenyl)-2-oxoimidazolidin-1-yl)benzaldehyde

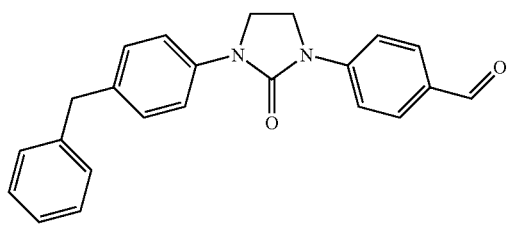

The title compound was prepared as Compound 1 (step 5 in scheme 1) in the general method described above (67% yield): $^1$H NMR (400 MHz, $CDCl_3$) δ 9.92 (s, 1H), 7.88 (br d, J=8.0, 2H), 7.78 (br d, J=7.4, 2H), 7.50 (br d, J=8.2, 2H), 7.31-7.18 (m, 7H), 3.98 (br s, 6H). MS (ESI) m/z: Calculated: 356.42; Observed: 357.2 ($M^+$+1).

1-(4-(3-(4-benzylphenyl)-2-oxoimidazolidin-1-yl)benzyl)azetidine-3-carboxylic acid

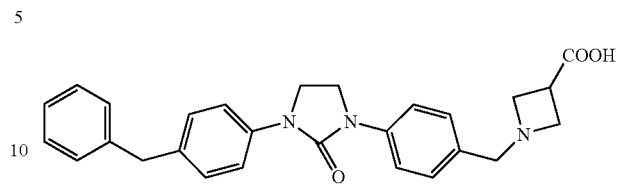

The title compound was prepared as Example Compound 1 (step 6) described above (% yield): $^1$H NMR (400 MHz, $CDCl_3$): δ 8.04 (d, 2H), 7.68 (d, 2H), 7.50 (d, 2H), 7.35-7.18 (m, 7H), 3.98 (m, 4H), 3.90-3.80 (m, 8H), 3.61 (m, 1H). MS (ESI) m/z: Calculated: 441.21; Observed: 442.00 ($M^+$+1).

Compound 7

1-(4-(3-(biphenyl-4-yl)-2-oxoimidazolidin-1-yl)benzyl)azetidine-3-carboxylic acid (Scheme 1)

Methyl 4-(3-(biphenyl-4-yl)-2-oxoimidazolidin-1-yl)benzoate

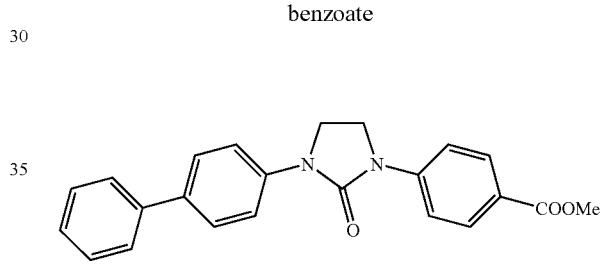

The title compound was prepared as Example Compound 1 (step 3) described above (73% yield): $^1$H NMR (400 MHz, $CDCl_3$) δ 7.74-7.21 (m, 13H), 3.95 (s, 4H), 3.90 (s, 3H). MS (ESI) m/z: Calculated: 372.15; Observed: 372.9 ($M^+$+1).

1-(biphenyl-4-yl)-3-(4-(hydroxymethyl)phenyl)imidazolidin-2-one

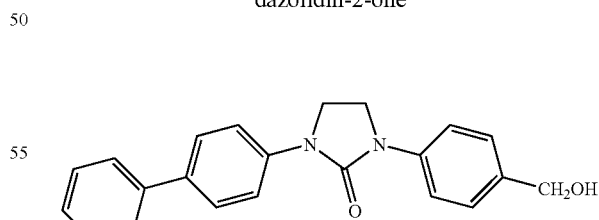

The title compound was prepared as Example Compound 1 (step 4) described above (40% yield): $^1$H NMR (400 MHz, $CDCl_3$) δ 7.62 (d, 2H), 7.42-7.23 (m, 7H), 7.06 (d, 4H), 4.62 (s, 2H), 3.84 (m, 4H). MS (ESI) m/z: Calculated: 344.15; Observed: 344.9 ($M^+$+1).

4-(3-(biphenyl-4-yl)-2-oxoimidazolidin-1-yl)benzaldehyde

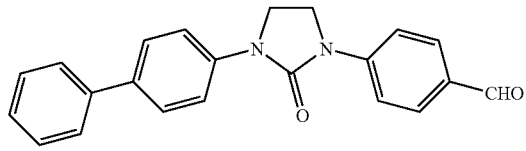

The title compound was prepared as Example Compound 1 (step 5) described above (62% yield): $^1$H NMR (400 MHz, CDCl$_3$) δ 10.00 (s, 1H), 7.77 (d, 2H), 7.69-7.43 (m, 9H), 7.36 (d, 2H), 4.02 (s, 4H). MS (ESI) m/z: Calculated: 342.14; Observed: 343.1 (M$^+$+1).

1-(4-(3-(biphenyl-4-yl)-2-oxoimidazolidin-1-yl)benzyl)azetidine-3-carboxylic acid

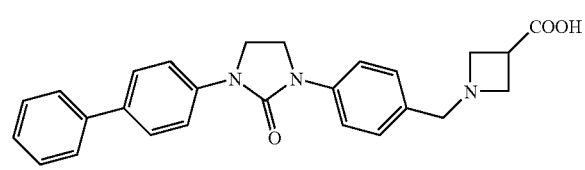

The title compound was prepared as Example Compound 1 (step 6) described above (5% yield): MS (ESI) m/z: Calculated: 427.19; Observed: 427.9 (M$^+$+1).

Compound 8

1-(4-(3-(3-Cyclohexylphenyl)-2-oxoimidazolidin-1-yl)benzyl)azetidine-3-carboxylic acid (Scheme 3)

Methyl 4-(3-(3-bromophenyl)-2-oxoimidazolidin-1-yl)benzoate and methyl 4-(3-(3-iodophenyl)-2-oxoimidazolidin-1-yl)benzoate

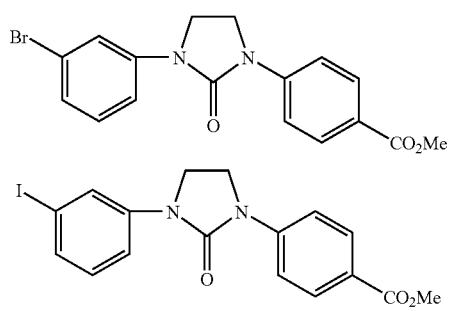

The title compounds were prepared using a procedure analogous to Compound 1 (step 3) described above as a mixture without further separation (48% yield):

Methyl 4-(3-(3-cyclohexylphenyl)-2-oxoimidazolidin-1-yl)benzoate

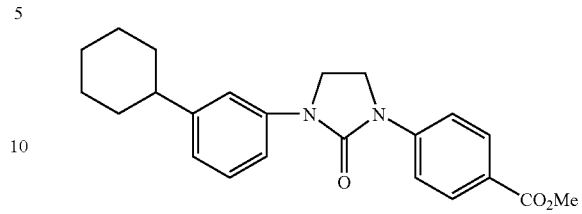

A mixture of ethyl 4-(3-(3-bromophenyl)-2-oxoimidazolidin-1-yl)benzoate and methyl 4-(3-(3-iodophenyl)-2-oxoimidazolidin-1-yl)benzoate (190 mg, ~0.5 mmol) was dissolved in a tetrahydrofuran (THF) solution of Rieke's reagent (0.5M, 1.5 mmol) in a microwave reaction tube. Pd(P$^t$Bu$_3$)$_2$ (13 mg, 0.03 mmol) was added to this solution. The mixture was purged with N$_2$ gas for 3-5 minutes and heated at 100° C. for 30 minutes under microwave irradiation (Personal Chemistry Emrys™ Optimizer microwave reactor). Upon completion of the reaction, the reaction mixture was diluted with ethyl acetate, brine, filtered through Celite. The filtrate was dried over Na$_2$SO$_4$ and concentrated. The residue was purified by silica gel column chromatography (ISCO system, 1% MeOH/dichloromethane) to give a pure product (155 mg, 81% yield): $^1$H NMR (400 MHz, DMSO-d$_6$) δ 7.95 (m, 2H), 7.78 (m, 2H), 7.55 (s, 1H), 7.38 (dd, 1H), 7.28 (dd, 1H), 6.95 (d, 1H), 4.00 (s, 4H), 3.81 (s, 3H), 2.45 (m, 1H, under the peak of DMSO-d$_6$), 1.67-1.79 (m, 5H), 1.21-1.45 (m, 5H). MS (ESI) m/z: Calculated: 378.19; Observed: 379.2 (M$^+$+1).

1-(3-Cyclohexylphenyl)-3-(4-(hydroxymethyl)phenyl)imidazolidin-2-one

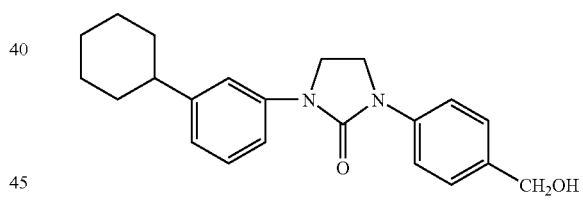

The title compound was prepared as Example Compound 1 (step 4) described above (71% yield): $^1$H NMR (400 MHz, DMSO-d$_6$) δ 7.59 (m, 3H), 7.37 (d, 1H), 7.22-7.29 (m, 3H), 6.92 (d, 1H), 5.13 (dd, 1H), 4.45 (d, 2H), 3.94 (s, 4H), 2.45 (m, 1H, under the peak of DMSO-d$_6$), 1.67-1.79 (m, 5H), 1.20-1.45 (m, 5H).

4-(3-(3-Cyclohexylphenyl)-2-oxoimidazolidin-1-yl)benzaldehyde

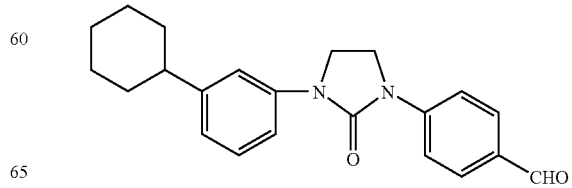

The title compound was prepared as Example Compound 1 (step 5) described above (65% yield): ¹H NMR (400 MHz, CDCl₃) δ 9.91 (s, 1H), 7.88 (d, 2H), 7.79 (d, 2H), 7.56 (s, 1H), 7.28 (m, 2H), 6.99 (d, 1H), 4.02 (s, 4H), 2.53 (m, 1H), 1.66-1.90 (m, 5H), 1.23-1.49 (m, 5H). MS (ESI) m/z: Calculated: 348.18; Observed: 349.3 (M⁺+1).

1-(4-(3-(3-Cyclohexylphenyl)-2-oxoimidazolidin-1-yl)benzyl)azetidine-3-carboxylic acid

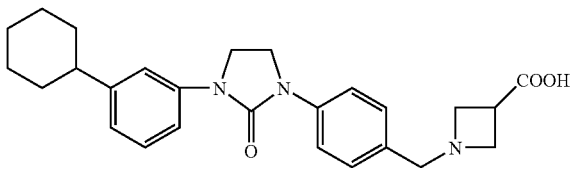

The title compound was prepared as Example Compound 1 (step 6) described above (15% yield): ¹H NMR (400 MHz, CDOD₃) δ 7.75 (d, 2H), 7.49 (m, 3H), 7.36 (d, 1H), 7.28 (dd, 1H), 7.00 (d, 1H), 4.37 (s, 2H), 4.31 (m, 4H), 4.00 (s, 4H), 3.68 (m, 1H), 2.53 (m, 1H), 1.76-1.87 (m, 5H), 1.32-1.50 (m, 5H). MS (ESI) m/z: Calculated: 433.24; Observed: 433.90 (M⁺+1).

Compound 9

1-(4-(3-(3-Benzylphenyl)-2-oxoimidazolidin-1-yl)-3-fluorobenzyl)azetidine-3-carboxylic acid (Scheme 3)

Methyl 3-fluoro-4-(2-oxoimidazolidin-1-yl)benzoate

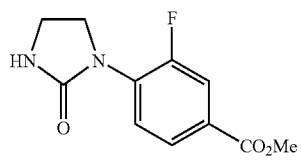

The title compound was prepared as Example Compound 1 (step 1) described above (57% yield): ¹H NMR (400 MHz, CDCl₃) δ 7.78 (m, 3H), 4.06 (dd, 2H), 3.92 (s, 3H), 3.61 (dd, 2H).

Methyl 4-(3-(3-bromophenyl)-2-oxoimidazolidin-1-yl)-3-fluorobenzoate and methyl 3-fluoro-4-(3-(3-iodophenyl)-2-oxoimidazolidin-1-yl)benzoate

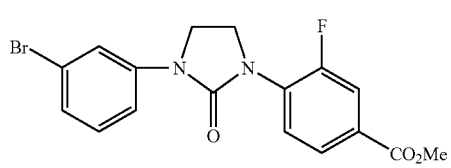

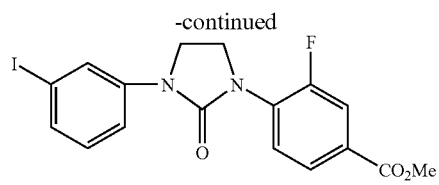

The title compounds were prepared using a procedure analogous to Compound 1 (step 3) described above as a mixture without further separation for the next step (60% yield):

Methyl 4-(3-(3-benzylphenyl)-2-oxoimidazolidin-1-yl)-3-fluorobenzoate

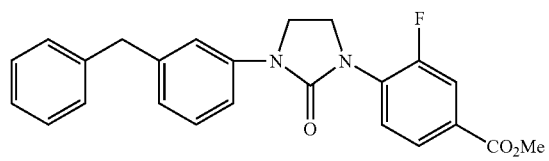

The title compound was prepared as Example Compound 7 (step 2) described above (63% yield): ¹H NMR (400 MHz, CDCl₃) δ 7.80 (m, 2H), 7.50 (s, 1H), 7.17-7.40 (m, 8H), 6.95 (d, 1H), 4.10 (m, 2H), 4.00 (s, 2H), 3.90 (m, 2H), 3.85 (s, 3H). MS (ESI) m/z: Calculated: 404.15; Observed: 405.3 (M⁺+1).

1-(3-Benzylphenyl)-3-(2-fluoro-4-(hydroxymethyl)phenyl)imidazolidin-2-one

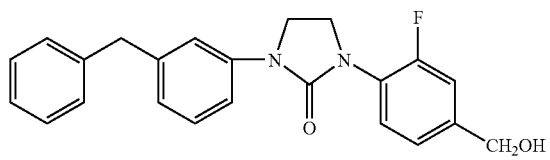

The title compound was prepared as Example Compound 1 (step 4) described above (68% yield): ¹H NMR (400 MHz, CDCl₃) δ 7.52 (dd, 2H), 7.41 (d, 1H), 7.29 (m, 3H), 7.11-7.21 (m, 5H), 6.92 (d, 1H), 4.67 (d, 2H), 4.00 (s, 2H), 3.96 (s, 4H). MS (ESI) m/z: Calculated: 376.16; Observed: 377.2 (M⁺+1).

4-(3-(3-Benzylphenyl)-2-oxoimidazolidin-1-yl)-3-fluorobenzaldehyde

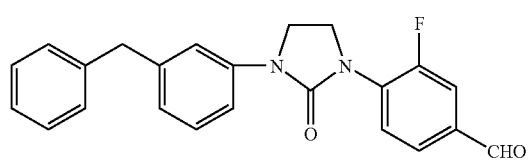

The title compound was prepared as Example Compound 1 (step 5) described above (69% yield): ¹H NMR (400 MHz, CDCl₃) δ 9.90 (s, 1H), 7.94 (dd, 1H), 7.66 (m, 2H), 7.49 (s, 1H), 7.40 (d, 1H), 7.29 (m, 3H), 7.21 (m, 3H), 6.96 (d, 1H), 4.11 (m, 2H), 4.00 (s, 2H), 3.96 (m, 2H). MS (ESI) m/z: Calculated: 374.41; Observed: 375.1 (M$^+$+1).

1-(4-(3-(3-Benzylphenyl)-2-oxoimidazolidin-1-yl)-3-fluorobenzyl)azetidine-3-carboxylic acid

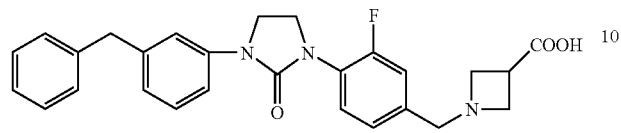

The title compound was prepared as Example Compound 1 (step 6) described above (38% yield): $^1$H NMR (400 MHz, CDOD$_3$) δ 7.66 (dd, 1H), 7.48 (s, 1H), 7.14-7.41 (m, 9H), 6.97 (d, 1H), 4.42 (s, 2H), 4.35 (m, 4H), 4.04 (s, 4H), 3.97 (s, 2H), 3.70 (m, 1H). MS (ESI) m/z: Calculated: 459.51; Observed: 460.0 (M$^+$+1).

Compound 10

1-(4-(3-(3-Cyclohexylphenyl)-2-oxoimidazolidin-1-yl)-3-fluorobenzyl)azetidine-3-carboxylic acid
(Scheme 3)

Methyl 4-(3-(3-cyclohexylphenyl)-2-oxoimidazolidin-1-yl)-3-fluorobenzoate

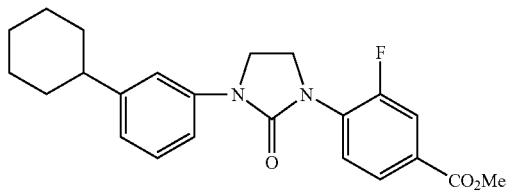

The title compound was prepared as Example Compound 7 (step 2) described above (84% yield): $^1$H NMR (400 MHz, CDCl$_3$) δ 7.80 (m, 3H), 7.58 (s, 1H), 7.30 (m, 2H), 6.98 (s, 1H), 4.10 (m, 2H), 4.05 (m, 2H), 3.92 (s, 3H), 2.60 (m, 1H), 1.25-1.85 (m, 10H). MS (ESI) m/z: Calculated: 396.18; Observed: 397.3 (M$^+$+1).

1-(3-Cyclohexylphenyl)-3-(2-fluoro-4-(hydroxymethyl)phenyl)imidazolidin-2-one

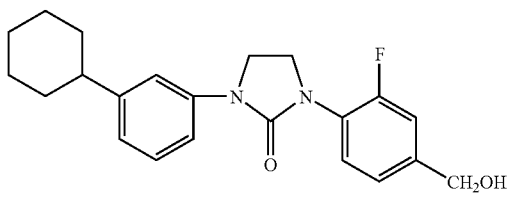

The title compound was prepared as Example Compound 1 (step 4) described above (40% yield): MS (ESI) m/z: Calculated 368.19; Observed: 369.3 (M$^+$+1).

4-(3-(3-Cyclohexylphenyl)-2-oxoimidazolidin-1-yl)-3-fluorobenzaldehyde

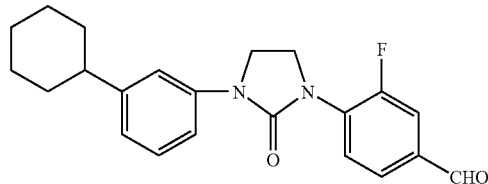

The title compound was prepared as Example Compound 1 (step 5) described above (53% yield): $^1$H NMR (400 MHz, CDCl$_3$) δ 9.90 (s, 1H), 7.99 (dd, 1H), 7.70 (m, 2H), 7.63 (s, 1H), 7.29 (m, 2H), 6.99 (m, 1H), 4.13 (m, 2H), 4.03 (m, 2H), 2.53 (m, 1H), 1.72-1.90 (m, 5H), 1.23-1.50 (m, 5H). MS (ESI) m/z: Calculated: 366.17; Observed: 367.2 (M$^+$+1).

1-(4-(3-(3-Cyclohexylphenyl)-2-oxoimidazolidin-1-yl)-3-fluorobenzyl)azetidine-3-carboxylic acid

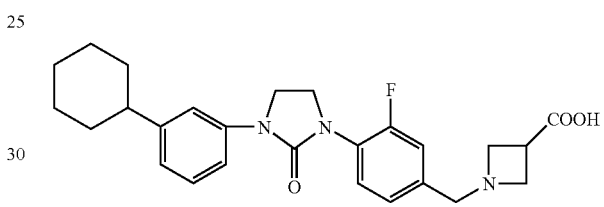

The title compound was prepared as Example Compound 1 (step 6) described above (35% yield): $^1$H NMR (400 MHz, CDOD$_3$) δ 7.67 (d, 1H), 7.49 (s, 1H), 7.37 (m, 4H), 7.27 (dd, 1H), 7.00 (d, 1H), 4.42 (s, 2H), 4.35 (m, 4H), 4.07 (s, 4H), 3.68 (m, 1H), 2.52 (m, 1H), 1.74-1.88 (m, 5H), 1.28-1.52 (m, 5H). MS (ESI) m/z: Calculated: 451.23; Observed: 452.1 (M$^+$+1).

EQUIVALENTS

Those skilled in the art will recognize, or be able to ascertain using no more than routine experimentation, numerous equivalents to the specific procedures described herein. Such equivalents are considered to be within the scope of the invention. Various substitutions, alterations, and modifications may be made to the invention without departing from the spirit and scope of the invention. Other aspects, advantages, and modifications are within the scope of the invention. The contents of all references, issued patents, and published patent applications cited throughout this application are hereby incorporated by reference. The appropriate components, processes, and methods of those patents, applications and other documents may be selected for the invention and embodiments thereof.

What is claimed is:
1. A compound having the formula:

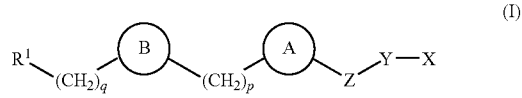

(I)

or pharmaceutically acceptable salts thereof;

wherein, p and q are independently 0, 1, 2, 3 or 4;

Z is O, $NR^2$, S, S(O), $S(O)_2$, $S(O)_2NR^2$, $(CR^3R^4)_n$, C=O, C=S, or C=N—$R^2$;

n is 1, 2, 3 or 4;

$R^1$ is aryl or heteroaryl;

$R^2$ is hydrogen, hydroxyl, $S(O)_2$, C=O, C=S, C=NH, $C_{1-6}$ alkyl, $C_{1-5}$ alkoxy, $C_{1-5}$ alkylthio, halo-substituted $C_{1-6}$ alkyl, halo-substituted $C_{1-5}$ alkoxy, aryl, or heteroaryl;

$R^3$ and $R^4$ are independently hydrogen, halo, hydroxyl, cyano, $C_{1-6}$ alkyl, $C_{1-5}$ alkoxy, $C_{1-5}$ alkylthio, halo-substituted $C_{1-6}$ alkyl, halo-substituted $C_{1-5}$ alkoxy, aryl, or heteroaryl; or $R^3$ and $R^4$, taken together, may form C=O;

X is $WC(O)OR^{5a}$, $WP(O)R^{5b}R^{5c}$, $WS(O)_2OH$, $WS(O)_2NH_2$, $WCONHSO_3H$ or 1H-tetrazol-5-yl;

W is a direct bond, O, or $C_{1-4}$ alkylene optionally substituted with one or more of halo, hydroxyl, cyano, amino, alkylamino, aryl amino, heteroaryl amino group, $C_{1-4}$ alkoxy, or $CO_2H$;

$R^{5a}$ is hydrogen or $C_{1-4}$ alkyl;

$R^{5b}$ and $R^{5c}$ are independently hydrogen, hydroxyl, $C_{1-4}$ alkyl, or halo substituted $C_{1-4}$ alkyl;

Y is

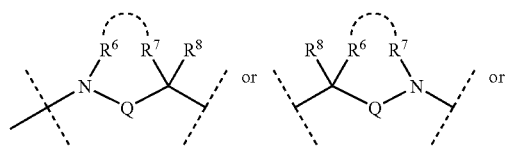

;

Q is a direct bond, C=O, C=S, $SO_2$, $C(O)NR^9$, or $(CR^9R^{10})_m$;

m is 0 or 1;

$R^6$ and $R^7$ are independently hydrogen, halo, hydroxyl, cyano, $C_{1-6}$ alkyl, $C_{1-5}$ alkylthio, $C_{1-5}$ alkoxy, halo-substituted $C_{1-6}$ alkyl or halo-substituted $C_{1-5}$ alkoxy; or $R^6$ and $R^7$ may be joined together with the atoms to which they are attached to form a 4- to 7-membered ring, or $R^6$ is an alkylene group with the omega end of said alkylene group attached to ring A;

$R^8$ is hydrogen, halogen, hydroxyl, amino, cyano, $C_{1-6}$ alkyl, $C_{1-5}$ alkylthio, $C_{1-5}$ alkoxy, halo-substituted $C_{1-6}$ alkyl, or halo-substituted $C_{1-5}$ alkoxy;

$R^9$ and $R^{10}$ are independently hydrogen, halo, hydroxyl, cyano, $C_{1-6}$ alkyl, $C_{1-5}$ alkoxy, $C_{1-5}$ alkylthio, halo-substituted $C_{1-6}$ alkyl, halo-substituted $C_{1-5}$ alkoxy, or —$CO_2R^{5a}$;

A is aryl or heteroaryl, either of which may optionally be substituted with 1, 2, or 3 substituents selected from the group consisting of halo, hydroxyl, cyano, $C_{1-6}$ alkyl, $C_{1-5}$ alkylthio, $C_{1-5}$ alkoxy, halo-substituted $C_{1-6}$ alkyl, and halo-substituted $C_{1-5}$ alkoxy;

B has the formula:

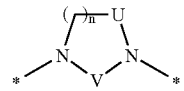

in which, the asterisks indicate the point of attachment in formula I;

r is 1;

U is $CH_2$, $C(H)CH_3$, $C(CH_3)_2$, $C(H)(CF_3)$ or $C(CF_3)_2$; and

V is C(=O) or C(=S).

2. The compound of claim 1, wherein Z is $(CR^3R^4)_n$.

3. The compound of claim 1, wherein X is $WC(O)OR^{5a}$.

4. The compound of claim 1, wherein Y is

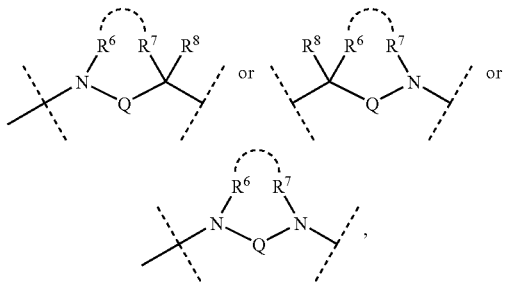

Q is $(CR^9R^{10})_m$, and $R^6$ and $R^7$ are joined together with the atoms to which they are attached to form a 4- to 7-membered ring.

5. The compound of claim 1, wherein Y is

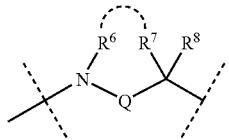

Q is $(CR^9R^{10})_m$, and $R^6$ and $R^7$ are joined together with the atoms to which they are attached to form a 4- to 7-membered ring.

6. The compound of claim 1, wherein V is C(=O) and Z is $(CR^3R^4)_n$.

7. A compound having the formula II:

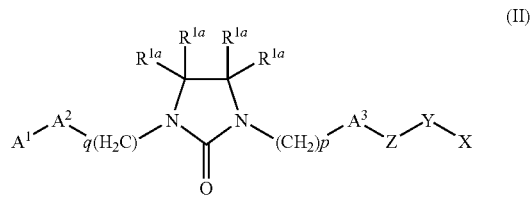

or a pharmaceutically acceptable salt thereof;

wherein, $A^1$ is H, $C_{1-8}$ alkyl, cycloalkyl, haloalkyl, aryl, aralkyl, —$OR^2$, —$SR^2$, —$S(O)R^2$, —$S(O)_2R^2$; —$C(O)R^2$, —$CO_2R^2$, or —$C(R^3)_2R^2$;

A² is 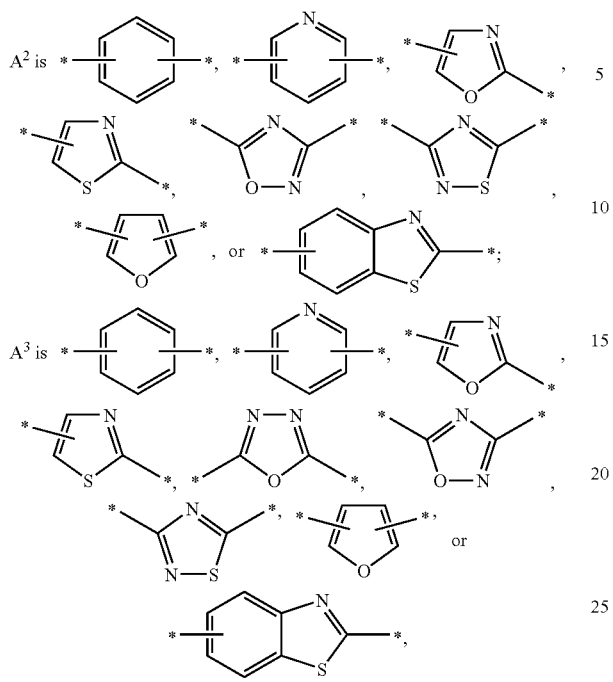

, each of which may optionally be substituted with a halogen, trifluoromethyl, or alkoxy;

p and q represent independently 0, 1, 2, 3 or 4;
Z is $(CR^3R^4)_n$ or C(O);
n is 1, 2, 3 or 4;
$R^{1a}$ is H or $C_{1-6}$ alkyl;
$R^2$ is alkyl, aryl, heteroaryl, or aralkyl;
$R^3$ and $R^4$ represent independently for each occurrence hydrogen, halo, hydroxyl, $C_{1-6}$ alkyl, $C_{1-5}$ alkoxy, or aryl;
X is $WC(O)OR^5$ or $WS(O)_2NH_2$;
$R^5$ is hydrogen or $C_{1-4}$ alkyl;
W is a direct bond, oxygen or $C_{1-4}$ alkylene;
Y is

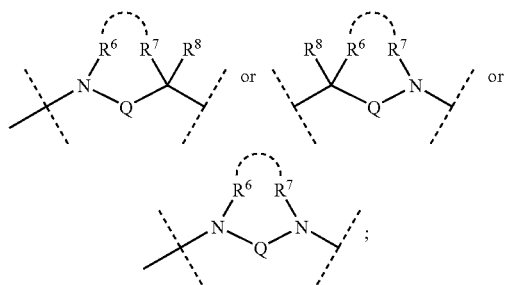

Q is a direct bond, C=O or $(CR^9R^{10})_m$;
m is 1;
$R^6$ and $R^7$ each represent independently hydrogen, halo, hydroxyl, $C_{1-6}$ alkyl, or $C_{1-5}$ alkoxy; or $R^6$ and $R^7$ may be joined together with the atoms to which they are attached to form a 4- to 7-membered ring;
$R^8$ is hydrogen, halogen, hydroxyl, amino, $C_{1-6}$ alkyl, or $C_{1-5}$ alkoxy; and
$R^9$ and $R^{10}$ each independently represent hydrogen, halo, $C_{1-6}$ alkyl, or $-CO_2R^5$.

8. The compound of claim 7, wherein A² is

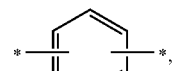

A³ is

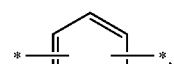

and Y is

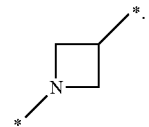

9. The compound of claim 1, wherein the pharmaceutically acceptable salt is selected from the group consisting of hydrochloride, maleate, citrate, fumarate, succinate, tartarate, mesylate, sodium, potassium, magnesium, and calcium salts.

10. The compound of claim 1, wherein the compound is selected from the group consisting of
1-(4-(3-(4-tert-butylphenyl)-2-oxoimidazolidin-1-yl)benzyl)azetidine-3-carboxylic acid,
1-(4-(3-(4-tert-butylbenzyl)-2-oxoimidazolidin-1-yl)benzyl)azetidine-3-carboxylic acid,
1-(4-(3-(4-butylphenyl)-2-oxoimidazolidin-1-yl)benzyl)azetidine-3-carboxylic acid,
1-(4-(3-(3-tert-butylphenyl)-2-oxoimidazolidin-1-yl)benzyl)azetidine-3-carboxylic acid,
1-(4-(2-oxo-3-(3-(trifluoromethyl)phenyl)imidazolidin-1-yl)benzyl)azetidine-3-carboxylic acid,
1-(4-(3-(4-benzylphenyl)-2-oxoimidazolidin-1-yl)benzyl)azetidine-3-carboxylic acid,
1-(4-(3-(biphenyl-4-yl)-2-oxoimidazolidin-1-yl)benzyl)azetidine-3-carboxylic acid,
1-(4-(3-(3-cyclohexylphenyl)-2-oxoimidazolidin-1-yl)benzyl)azetidine-3-carboxylic acid,
1-(4-(3-benzylphenyl)-2-oxoimidazolidin-1-yl)-3-fluorobenzyl)azetidine-3-carboxylic acid, and 1-(4-(3-(3-cyclohexylphenyl)-2-oxoimidazolidin-1-yl)-3-fluorobenzyl)azetidine-3-carboxylic acid, or pharmaceutically acceptable salts thereof.

11. A compound selected from the group consisting of
1-(4-(3-(3-benzoylphenyl)-2-oxoimidazolidin-1-yl)benzyl)azetidine-3-carbo-xylic acid;
1-(4-(2-oxo-3-(3-(1-phenylethyl)phenyl)imidazolidin-1-yl)benzyl)azetidine-3-carboxylic acid;
1-(4-(3-(3-(hydroxy(phenyl)methyl)phenyl)-2-oxoimidazolidin-1-yl)benzyl)azetidine-3-carboxylic acid;
1-(4-(3-(3-(difluoro(phenyl)methyl)phenyl)-2-oxoimidazolidin-1-yl)benzyl)-azetidine-3-carboxylic acid;
1-(4-(2-oxo-3-(3-phenoxyphenyl)imidazolidin-1-yl)benzyl)azetidine-3-carbo-xylic acid;
1-(4-(3-(3-(cyclobutylmethoxy)phenyl)-2-oxoimidazolidin-1-yl)-3-fluorobenzyl)azetidine-3-carboxylic acid;

1-(4-(3-(3-(cyclopropylmethoxy)phenyl)-2-oxoimidazolidin-1-yl)-3-fluorobenzyl)azetidine-3-carboxylic acid;
1-(4-(3-(4-cyclohexylpyridin-2-yl)-2-oxoimidazolidin-1-yl)benzyl)azetidine-3-carboxylic acid,
1-(4-(3-(5-cyclohexylpyridin-3-yl)-2-oxoimidazolidin-1-yl)benzyl)azetidine-3-carboxylic acid;
1-(4-(3-(2-cyclohexylpyridin-4-yl)-2-oxoimidazolidin-1-yl)benzyl)azetidine-3-carboxylic acid;
1-(4-(2-oxo-3-(3-(phenylsulfonyl)phenyl)imidazolidin-1-yl)benzyl)azetidine-3-carboxylic acid;
1-(4-(2-oxo-3-(3-(phenylsulfinyl)phenyl)imidazolidin-1-yl)benzyl)azetidine-3-carboxylic acid;
1-(4-(2-oxo-3-(3-(phenylthio)phenyl)imidazolidin-1-yl)benzyl)azetidine-3-carboxylic acid;
1-(4-(3-(3-(2-fluorobenzyl)phenyl)-2-oxoimidazolidin-1-yl)benzyl)azetidine-3-carboxylic acid;
1-(4-(3-(3-(3-fluorobenzyl)phenyl)-2-oxoimidazolidin-1-yl)benzyl)azetidine-3-carboxylic acid;
1-(4-(3-(3-(4-fluorobenzyl)phenyl)-2-oxoimidazolidin-1-yl)benzyl)azetidine-3-carboxylic acid;
1-(4-(3-(5-cyclohexyl-1,2,4-oxadiazol-3-yl)-2-oxoimidazolidin-1-yl)benzyl)azetidine-3-carboxylic acid;
1-(4-(3-(4-cyclohexyloxazol-2-yl)-2-oxoimidazolidin-1-yl)benzyl)azetidine-3-carboxylic acid;
1-(4-(3-(3-cyclohexyl-1,2,4-thiadiazol-5-yl)-2-oxoimidazolidin-1-yl)benzyl)azetidine-3-carboxylic acid;
1-(4-(3-(3-(cyclohexyloxymethyl)phenyl)-2-oxoimidazolidin-1-yl)benzyl)azetidine-3-carboxylic acid;
1-(4-(3-(5-methylbenzo[d]thiazol-2-yl)-2-oxoimidazolidin-1-yl)benzyl)azetidine-3-carboxylic acid;
1-(4-(3-(3-cyclohexyl-1,2,4-oxadiazol-5-yl)-2-oxoimidazolidin-1-yl)benzyl)azetidine-3-carboxylic acid;
1-(4-(3-(4-cyclohexylfuran-2-yl)-2-oxoimidazolidin-1-yl)benzyl)azetidine-3-carboxylic acid;
1-(4-(3-(4-cyclohexylthiazol-2-yl)-2-oxoimidazolidin-1-yl)benzyl)azetidine-3-carboxylic acid;
1-(4-(3-(3-cyclohexylphenyl)-2-oxoimidazolidin-1-yl)benzyl)pyrrolidine-3-carboxylic acid;
2-amino-3-(4-(3-(3-cyclohexylphenyl)-2-oxoimidazolidin-1-yl)benzylamino)propanoic acid;
3-amino-1-(4-(3-(3-cyclohexylphenyl)-2-oxoimidazolidin-1-yl)benzyl)azetidine-3-carboxylic acid;
1-(4-(3-(3-cyclohexylphenyl)-2-oxoimidazolidin-1-yl)benzyl)-3-hydroxyazetidine-3-carboxylic acid;
1-(4-(((2H-tetrazol-5-yl)azetidin-1-yl)methyl)phenyl)-3-(3-cyclohexylphenyl)imidazolidin-2-one;
3-(4-(3-(3-cyclohexylphenyl)-2-oxoimidazolidin-1-yl)benzylamino)propanoic acid;
4-(4-(3-(3-cyclohexylphenyl)-2-oxoimidazolidin-1-yl)benzylamino)butanoic acid;
3-((4-(3-(3-cyclohexylphenyl)-2-oxoimidazolidin-1-yl)benzyl)(methyl)amino)propanoic acid;
4-(4-(3-(3-cyclohexylphenyl)-2-oxoimidazolidin-1-yl)benzylamino)-4-oxobutanoic acid;
2-(4-(3-(3-cyclohexylphenyl)-2-oxoimidazolidin-1-yl)benzylamino)succinic acid;
3-(6-(3-(3-cyclohexylphenyl)-2-oxoimidazolidin-1-yl)-3,4-dihydroisoquinolin-2(1H)-yl)propanoic acid;
2-(4-(3-(3-cyclohexylphenyl)-2-oxoimidazolidin-1-yl)benzylamino)ethanesulfonamide;
1-((6-(3-(3-cyclohexylphenyl)-2-oxoimidazolidin-1-yl)pyridin-3-yl)methyl)-azetidine-3-carboxylic acid;
1-((5-(3-(3-cyclohexylphenyl)-2-oxoimidazolidin-1-yl)pyridin-2-yl)methyl)-azetidine-3-carboxylic acid;
1-(4-(3-(3-cyclohexylphenyl)-2-oxoimidazolidin-1-yl)-3-fluorobenzyl)azetidine-3-carboxylic acid;
1-(4-(3-(3-cyclohexylphenyl)-2-oxoimidazolidin-1-yl)-3-(trifluoromethyl)benzyl)azetidine-3-carboxylic acid;
1-(4-(3-(3-cyclohexylphenyl)-2-oxoimidazolidin-1-yl)-3-methoxybenzyl)azetidine-3-carboxylic acid;
1-(4-(3-(3-cyclohexylphenyl)-2-oxoimidazolidin-1-yl)-2-fluorobenzyl)azetidine-3-carboxylic acid;
1-((5-(3-(3-cyclohexylphenyl)-2-oxoimidazolidin-1-yl)thiazol-2-yl)methyl)azetidine-3-carboxylic acid;
1-((5-(3-(3-cyclohexylphenyl)-2-oxoimidazolidin-1-yl)-1,3,4-oxadiazol-2-yl)methyl)azetidine-3-carboxylic acid;
1-((5-(3-(3-cyclohexylphenyl)-2-oxoimidazolidin-1-yl)benzo[d]thiazol-2-yl)methyl)azetidine-3-carboxylic acid;
1-((6-(3-(3-cyclohexylphenyl)-2-oxoimidazolidin-1-yl)thiazolo[5,4-b]pyridin-2-yl)methyl)azetidine-3-carboxylic acid;
1-((6-(3-(3-cyclohexylphenyl)-2-oxoimidazolidin-1-yl)oxazolo[5,4-b]pyridin-2-yl)methyl)azetidine-3-carboxylic acid;
1-((5-(3-(3-cyclohexylphenyl)-2-oxoimidazolidin-1-yl)furo[2,3-b]pyridin-2-yl)methyl)azetidine-3-carboxylic acid;
1-((5-(3-(3-cyclohexylphenyl)-2-oxoimidazolidin-1-yl)benzofuran-2-yl)methyl)azetidine-3-carboxylic acid;
1-(4-(3-(3-cyclohexyl-4-(trifluoromethyl)phenyl)-2-oxoimidazolidin-1-yl)benzyl)azetidine-3-carboxylic acid;
1-(4-(3-(4-cyclohexyl-3-(trifluoromethyl)phenyl)-2-oxoimidazolidin-1-yl)benzyl)azetidine-3-carboxylic acid;
1-(4-(3-(3-cyclohexylphenyl)-5-methyl-2-oxoimidazolidin-1-yl)benzyl)azetidine-3-carboxylic acid;
1-(4-(3-(3-cyclohexylphenyl)-4-methyl-2-oxoimidazolidin-1-yl)benzyl)azetidine-3-carboxylic acid;
1-(4-(3-(3-cyclohexylphenyl)-5,5-dimethyl-2-oxoimidazolidin-1-yl)benzyl)azetidine-3-carboxylic acid;
1-(4-(3-(3-cyclohexylphenyl)-2-oxo-5-(trifluoromethyl)imidazolidin-1-yl)benzyl)azetidine-3-carboxylic acid; and
1-(4-(3-(3-cyclohexylphenyl)-2-oxo-4-(trifluoromethyl)imidazolidin-1-yl)benzyl)azetidine-3-carboxylic acid; and pharmaceutically acceptable salts thereof.

* * * * *

UNITED STATES PATENT AND TRADEMARK OFFICE
CERTIFICATE OF CORRECTION

PATENT NO. : 7,790,707 B2 Page 1 of 1
APPLICATION NO. : 11/726356
DATED : September 7, 2010
INVENTOR(S) : Saha et al.

It is certified that error appears in the above-identified patent and that said Letters Patent is hereby corrected as shown below:

At column 68, line 5 (claim 1), replace 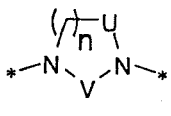 with 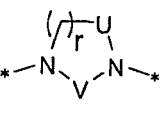 .

Signed and Sealed this
Fifth Day of April, 2011

David J. Kappos
*Director of the United States Patent and Trademark Office*